(12) United States Patent
Haj-Ahmad

(10) Patent No.: US 11,208,678 B2
(45) Date of Patent: *Dec. 28, 2021

(54) METHODS AND KITS FOR IMPROVING GLOBAL GENE EXPRESSION ANALYSIS OF HUMAN URINE DERIVED RNA

(71) Applicant: Norgen Biotek Corp., Thorold (CA)

(72) Inventor: Yousef Haj-Ahmad, St. Catharines (CA)

(73) Assignee: Norgen Biotek Corp., Thorold (CA)

( * ) Notice: Subject to any disclaimer, the term of this patent is extended or adjusted under 35 U.S.C. 154(b) by 613 days.

This patent is subject to a terminal disclaimer.

(21) Appl. No.: 16/042,282

(22) Filed: Jul. 23, 2018

(65) Prior Publication Data

US 2020/0024642 A1 Jan. 23, 2020

(51) Int. Cl.
*C12Q 1/6806* (2018.01)
*C12Q 1/6869* (2018.01)
*C12Q 1/6883* (2018.01)

(52) U.S. Cl.
CPC ......... *C12Q 1/6806* (2013.01); *C12Q 1/6869* (2013.01); *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 10,577,645 B2 * 3/2020 Haj-Ahmad ......... C12Q 1/6874
2015/0275267 A1 * 10/2015 O'Neil et al. ....... C12Q 1/6806 506/2
2017/0268040 A1 9/2017 Haj-Ahmads

OTHER PUBLICATIONS

Zhou et al., "A method for extracting and characterizing RNA from urine: For downstream PCR and RNAseq analysis," Anal. Biochem. 2017, 536:8-15. (Year: 2017).*
Abdelmaksoud-Dammak, Rania, et al., "Overexpression of miR-10b in colorectal cancer patients: Correlation with TWIST-1 and E-cadherin expression", Tumor Biol. 2017 39(3):1010428317695916.
Arai, Takayuki, et al., "Regulation of spindle and kinetochore-associated protein 1 by antitumor miR-10a-5p in renal cell carcinoma", Cancer Science 2017; 108(10): 2088-2101.
El-mogy, Mohamed, et al., "Diversity and signature of small RNA in different bodily fluids using next generation sequencing", BMC Genomics [Internet]. BMC Genomics; 2018;1-24. Available from: https://bmcgenomics.biomedcentral.com/articles/10.1186/s12864-018-4785-8.
Ma, Zhihong, et al., "Augmented miR-10b expression associated with depressed expression of its target gene KLF4 involved in gastric carcinoma", Int. J. Clin. Exp. Pathol. 2015; 8:5071-9.
Veerla, Srinivas, et al., "miRNA expression in urothelial carcinomas: Important roles of miR-10a, miR-222, miR-125b, miR-7 and miR-452 for tumor stage and metastasis, and frequent homozygous losses of miR-31", Int. J. Cancer 2009; 124: 2236-2242.
Xiao, Haibing, et al., "MicroRNA-10b promotes migration and invasion through KLF4 and HOXD10 in human bladder cancer", Oncol. Rep. 2014; 31:1832-8.
Zhang, Lin, et al., "MicroRNA-10b Triggers the Epithelial-Mesenchymal Transition (EMT) of Laryngeal Carcinoma Hep-2 Cells by Directly Targeting the E-cadherin", Appl. Biochem. Biotechnol. 2015; 176:33-44.
Zhou, Kun, et al., "A method for extracting and characterizing RNA from urine: For downstream PCR and RNAseq analysis", Anal. Biochem. 2017; 536:8-15.
"Homo sapiens miRNA 10a" (miRBase accession: MIMAT0000253).
"Homo sapiens miRNA 10b" (miRBase accession: MIMAT0000254).
Brenu, Ekua W., et al., "High-throughput sequencing of plasma microRNA in chronic fatigue syndrome/myalgic encephalomyelitis", PLoS One. Sep. 19, 2014; 9(9):e102783.
Chen, Hui, et al., "Expression and Prognostic Value of miR-486-5p in Patients with Gastric Adenocarcinoma", PLoS One. Mar. 20, 2015; 10(3): e0119384.
Dhahbi, Joseph M, et al. "5'-YRNA fragments derived by processing of transcripts from specific YRNA genes and pseudogenes are abundant in human serum and plasma", Physiol Genomics. Nov. 1, 2013;45(21):990-8.
Song, Libing, et al., "miR-486 sustains NF-κB activity by disrupting multiple NF-κB-negative feedback loops", Cell Research. Dec. 18, 2012; 23:274-289.
Tonge, DP and Gant, TW, "What is normal? Next generation sequencing-driven analysis of the human circulating miRNAome", BMC Molecular Biology. Feb. 9, 2016; 17:4.
MiRBase Accession No. MIMAT0002177.
NCBI Reference Sequence: NR_004393.1.

* cited by examiner

*Primary Examiner* — Kaijiang Zhang
(74) *Attorney, Agent, or Firm* — Coats & Bennett, PLLC

(57) ABSTRACT

Disclosed are methods and kits for improving global gene expression analysis for a population of RNA molecules derived from a human urine sample. In an embodiment, the method comprises the step of selectively depleting miR-10a-5p fragments from the population of RNA molecules or selectively blocking miR-10a-5p fragments within the RNA population. The miR-10a-5p depleted or miR-10a-5p blocked population of RNA can be used in a variety of global gene expression analysis protocols, including next generation sequencing. In a further embodiment, the method comprises selectively depleting or blocking miR-10b-5p fragments within the RNA population. The miR-10a-5p and/or miR-10b-5p depleted or blocked populations of RNA can also be used in global gene expression analysis protocols, including next generation sequencing. The kit comprises oligonucleotide probes comprising a nucleotide sequence that is the complement to a nucleotide sequence of the miR-10a-5p and/or oligonucleotide probes comprising a nucleotide sequence that is the complement to a nucleotide sequence of miR-10b-5p.

12 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 23
<212> TYPE: RNA
<213> ORGANISM: Artificial Sequence
<220> FEATURE:
<223> OTHER INFORMATION: miR-10a-5p fragment

<400> SEQUENCE: 1
uacccuguag auccgaauuu gug                                      23

<210> SEQ ID NO 2
<211> LENGTH: 23
<212> TYPE: DNA
<213> ORGANISM: Artificial Sequence
<220> FEATURE:
<223> OTHER INFORMATION: miR-10a-5p fragment capture probe

<400> SEQUENCE: 2
cacaaattcg gatctacagg gta                                      23

<210> SEQ ID NO 3
<211> LENGTH: 23
<212> TYPE: RNA
<213> ORGANISM: Artificial Sequence
<220> FEATURE:
<223> OTHER INFORMATION: miR-10b-5p fragment

<400> SEQUENCE: 3
uacccuguag aaccgaauuu gug                                      23

<210> SEQ ID NO 4
<211> LENGTH: 23
<212> TYPE: DNA
<213> ORGANISM: Artificial Sequence
<220> FEATURE:
<223> OTHER INFORMATION: miR-10b-5p fragment capture probe

<400> SEQUENCE: 4
cacaaattcg gttctacagg gta                                      23
```

METHODS AND KITS FOR IMPROVING GLOBAL GENE EXPRESSION ANALYSIS OF HUMAN URINE DERIVED RNA

FIELD OF INVENTION

The present invention provides a method of improving global gene expression analysis of human urine derived RNA, and in particular, the next generation sequencing of small RNA.

BACKGROUND

Global expression profiling of RNA and small RNA from various bodily fluids and tissue biopsies has become a staple approach for the monitoring and/or discovery of RNA biomarkers in various applications, including molecular diagnostics, dose/response effects studies, toxicity studies and other related applications. Global gene expression analysis can be carried out using a variety of methods including microarray analysis, library construction, reverse transcription, amplification, transcriptome profiling, expression analysis and sequencing, including next generation sequencing.

Human urine contains a variety of RNA molecules, which may be medically or scientifically relevant. The relative abundances of such RNA molecules can be indicative of donor health status or responses to various endogenous and exogenous stimuli. Of the RNA molecules present in human urine, a class of small non-coding, regulatory RNAs, called microRNA (miRNA), are of particular interest as biomarkers. Interest in miRNA as biomarkers is due to both their biological role in gene expression regulation and their relative stability in circulation (as compared to larger RNA molecules, which are more readily degraded).

Two miRNA molecules are abundant in the human urine miRNA milieu. These two molecules are: hsa-miR-10a and hsa-miR-10b (Zhou et al., 2017; El-Mogy et al., 2018). These molecules play a role in specific cancers such as colorectal cancer and renal cell carcinoma (Veerla et al., 2009; Xiao et al., 2014; Ma et al., 2015; Zhang et al., 2015; Abdelmaksoud-Dammak et al., 2017; Arai et al., 2017).

SUMMARY OF INVENTION

Disclosed are methods of improving global gene expression analysis for a population of RNA molecules derived from human urine. In one embodiment, the method comprises the step of depleting miR-10a-5p and/or miR-10b-5p from the population of RNA molecules. In another embodiment, the method comprises the step of blocking miR-10a-5p and/or miR-10b-5p fragments in the population of RNA molecules. The method provides a sample, in which the miR-10a-5p and/or miR-10b-5p fragments are preferably blocked by hybridization with complementary oligonucleotide probes. The resulting miR-10a-5p and/or miR-10b-5p depleted or blocked population of small RNA molecules can be used in variety of downstream global gene expression analysis, and in particular, next generation sequencing.

In one aspect, disclosed is a method of improving global gene expression analysis for a population of RNA molecules derived from human urine, the method comprising the step of depleting miR-10a-5p and/or miR-10b-5p fragments from the population of RNA molecules. The method may comprise depleting only miR-10a-5p fragments from the population of RNA molecules. The method may comprise depleting only miR-10b-5p fragments from the population of RNA molecules. The method may comprise depleting both miR-10a-5p and miR-10b-5p fragments from the population of RNA molecules.

In an embodiment of the method, the step of depleting miR-10a-5p fragments from the population of RNA molecules comprises:
  adding miR-10a-5p specific oligonucleotide probes to a sample containing the population of RNA molecules, wherein each miR-10a-5p specific probe comprises a nucleotide sequence that is the complement to a nucleotide sequence of miR-10a-5p;
  forming a complex between one or more miR-10a-5p fragments and a miR-10a-5p specific oligonucleotide probe; and
  removing the miR-10a-5p:oligonucleotide complexes from the sample.

Each miR-10a-5p specific oligonucleotide probe may comprise one or multiple copies of a nucleotide sequence that is the complement to the nucleotide sequence of the miR-10a-5p.

In another embodiment of the method, the step of depleting miR-10b-5p fragments from the population of RNA molecules comprises:
  adding miR-10b-5p specific oligonucleotide probes to a sample containing the population of RNA molecules, wherein each miR-10b-5p specific probe comprises a nucleotide sequence that is the complement to a nucleotide sequence of miR-10b-5p;
  forming a complex between one or more miR-10b-5p fragments and a miR-10b-5p specific oligonucleotide probe; and
  removing the miR-10b-5p:oligonucleotide complexes from the sample.

Each miR-10b-5p specific oligonucleotide probe may comprise one or multiple copies of a nucleotide sequence that is the complement to the nucleotide sequence of miR-10b-5p.

In another embodiment, the 5'end, the 3'end or both ends of each miR-10a-5p specific oligonucleotide probe or each miR-10b-5p specific oligonucleotide probe are modified, wherein the modification(s) facilitate the removal of the miR-10a-5p:oligonucleotide complexes and/or miR-10b-5p:oligonucleotide complexes from the sample.

In a further embodiment, each of the miR-10a-5p specific oligonucleotide probes and/or the miR-10b-5p specific oligonucleotide probes has a 5' biotin modification, a 3' biotin modification, a 5' dioxigenin modification, a 3' dioxigenin modification, and/or a 5' dinitrophenol modification.

In another embodiment, the miR-10a-5p specific oligonucleotide probes and/or the miR-10b-5p specific oligonucleotide probes are immobilized on a solid support.

In another aspect, disclosed is a method of improving global gene expression analysis for a population of RNA molecules derived from human urine, the method comprising the step of blocking miR-10a-5p and/or miR-10b-5p fragments in the population of RNA molecules. The method may comprise blocking only miR-10a-5p fragments in the population of RNA molecules. The method may comprise blocking only miR-10b-5p fragments in the population of RNA molecules. The method may comprise blocking both miR-10a-5p and miR-10b-5p fragments in the population of RNA molecules.

In an embodiment of the method, the step of blocking the miR-10a-5p fragments in the population of RNA molecules comprises:
  adding miR-10a-5p specific oligonucleotide probes to a sample containing the population of RNA molecules, wherein each miR-10a-5p specific oligonucleotide probe comprises a nucleotide sequence that is the complement to a nucleotide sequence of the miR-10a-5p; and forming a complex between one or more miR-10a-5p fragments and a miR-10a-5p specific oligonucleotide probe.

In another embodiment, the step of blocking the miR-10b-5p fragments in the population of RNA molecules comprises:

adding miR-10b-5p specific oligonucleotide probes to a sample containing the population of RNA molecules, wherein each miR-10b-5p specific oligonucleotide probe comprises a nucleotide sequence that is the complement to a nucleotide sequence of miR-10b-5p; and forming a complex between one or more miR-10b-5p fragments and a miR-10b-5p specific oligonucleotide probe.

In another embodiment, the 5'end, the 3'end or both ends of each miR-10a-5p specific oligonucleotide probe and/or miR-10b-5p specific oligonucleotide probe is modified to prevent ligation.

In a further embodiment, the 5'end or the 3'end of each miR-10a-5p specific oligonucleotide probe and/or miR-10b-5p specific oligonucleotide probe is modified by incorporating a dideoxy nucleotide.

In a further embodiment, the 5'end or the 3'end of each miR-10a-5p specific oligonucleotide probe and/or miR-10b-5p specific oligonucleotide probe is modified with biotin.

In a further embodiment, the 5'end of each miR-10a-5p specific oligonucleotide probe and/or miR-10b-5p specific oligonucleotide probe is modified with biotin and the 3'end of each miR-10a-5p specific oligonucleotide probe and/or miR-10b-5p specific oligonucleotide probe is modified by incorporating a dideoxy nucleotide.

In another embodiment of any of the methods described above, the global gene expression analysis can be microarray analysis, library construction, reverse transcription, amplification, transcriptome profiling, expression analysis and/or sequencing. In a further embodiment, the sequencing is next generation sequencing.

In another aspect, disclosed is a method of performing next generation sequencing of a population of small RNA derived from human urine, the method comprising:

adding miR-10a-5p specific oligonucleotide probes and/or miR-10b-5p specific oligonucleotide probes to a sample containing the population of RNA molecules, wherein each miR-10a-5p specific oligonucleotide probe comprises a nucleotide sequence that is the complement to a nucleotide sequence of miR-10a-5p and wherein each miR-10b-5p specific oligonucleotide probe comprises a nucleotide sequence that is the complement to a nucleotide sequence of miR-10b-5p;

forming a complex between one or more miR-10a-5p fragments and a miR-10a-5p specific oligonucleotide probe and/or forming a complex between one or more miR-10b-5p fragments and a miR-10b-5p specific oligonucleotide probe; and removing the miR-10a-5p:oligonucleotide complexes and/or miR-10b-5p:oligonucleotide complexes from the sample, wherein the remaining sample contains a miR-10a-5p and/or miR-10b-5p depleted population of small RNA molecules;

preparing a library using the remaining sample; and sequencing the library.

In one embodiment, only miR-10a-5p specific oligonucleotide probes are added and the remaining sample contains a miR-10a-5p depleted population of small RNA molecules. In another embodiment, only miR-10b-5p specific oligonucleotide probes are added and the remaining sample contains a miR-10b-5p depleted population of small RNA molecules. In a further embodiment, miR-10a-5p specific oligonucleotide probes and miR-10b-5p specific oligonucleotide probes are added and the remaining sample contains a miR-10a-5p and miR-10b-5p depleted population of small RNA molecules.

In another embodiment, each miR-10a-5p specific oligonucleotide probe comprises one or multiple copies of a nucleotide sequence that is the complement to the nucleotide sequence of the miR-10a-5p.

In another embodiment, each miR-10b-5p specific oligonucleotide probe comprises one or multiple copies of a nucleotide sequence that is the complement to the nucleotide sequence of miR-10b-5p.

In another embodiment, the miR-10a-5p:oligonucleotide complexes and/or miR-10b-5p:oligonucleotide complexes are removed by size exclusion chromatography.

In another embodiment, the miR-10a-5p:oligonucleotide complexes and/or miR-10b-5p:oligonucleotide complexes are removed by using silicon carbide.

In a further embodiment, the step of removing the miR-10a-5p:oligonucleotide complexes and/or miR-10b-5p:oligonucleotide complexes from the sample comprises:

combining the sample with a binding buffer, an alcohol and a silicon carbide slurry to provide a binding mixture, wherein the alcohol concentration of the binding mixture is about 1-30% (v/v) to affect selective binding of the miR-10a-5p:oligonucleotide complexes and/or miR-10b-5p:oligonucleotide complexes to the silicon carbide;

removing the miR-10a-5p:oligonucleotide complexes and/or miR-10b-5p:oligonucleotide complexes bound to SiC from the sample; and collecting the remaining sample containing the miR-10a-5p and/or miR-10b-5p depleted population of small RNA molecules.

In further embodiment, the step of removing the miR-10a-5p:oligonucleotide and/or miR-10b-5p:oligonucleotide complexes comprises:

combining the sample with a binding buffer and alcohol to provide a binding mixture;

applying the binding mixture to a silicon carbide column, wherein the alcohol concentration of the binding mixture is about 1-30% (v/v) to affect selective binding of the miR-10a-5p:oligonucleotide complexes and/or miR-10b-5p:oligonucleotide complexes to the silicon carbide;

collecting the column flowthrough containing the miR-10a-5p and/or miR-10b-5p depleted population of small RNA molecules.

The alcohol concentration of the binding mixture can be about 1-10% (v/v). In a further embodiment, the alcohol is ethanol.

In another embodiment, the 5'end, the 3'end or both ends of each miR-10a-5p specific oligonucleotide probe and/or miR-10b-5p specific oligonucleotide probe is modified and wherein the miR-10a-5p:oligonucleotide complexes and/or miR-10b-5p:oligonucleotide complexes are removed by:

selectively binding the miR-10a-5p:oligonucleotide complexes and/or miR-10b-5p:oligonucleotide complexes to a solid support comprising a protein or antibody that specifically interacts with an end modification on the miR-10a-5p specific oligonucleotide probe and/or miR-10b-5p specific oligonucleotide probe; and
collecting an unbound fraction of the sample containing the miR-10a-5p and/or miR-10b-5p depleted population of small RNA molecules.

In a further embodiment, the 5'end or the 3'end of each miR-10a-5p specific oligonucleotide probe and/or miR-10b-5p specific oligonucleotide probe is modified with biotin and the solid support comprises avidin or streptavidin.

In a further embodiment, the 5'end or the 3'end of each miR-10a-5p specific oligonucleotide probe and/or miR-10b-5p specific oligonucleotide probe is modified with digoxigenin and the solid support comprises digoxigenin specific antibodies.

In a further embodiment, the 5'end of each miR-10a-5p specific oligonucleotide probe and/or miR-10b-5p specific oligonucleotide probe is modified with dinitrophenol and the solid support comprises dinitrophenol specific antibodies.

In a further embodiment, the solid support comprises polymeric beads, which may be magnetic or non-magnetic.

In another aspect, disclosed is a method of performing next generation sequencing of a population of small RNA derived from human urine, the method comprising:
adding miR-10a-5p specific oligonucleotide probes and/or miR-10b-5p specific oligonucleotide probes to a sample containing the population of RNA molecules, wherein each miR-10a-5p specific oligonucleotide probe comprises a nucleotide sequence that is the complement to a nucleotide sequence of miR-10a-5p and wherein each miR-10b-5p specific oligonucleotide probe comprises a nucleotide sequence that is the complement to a nucleotide sequence of miR-10b-5p;
forming a complex between one or more miR-10a-5p fragments and a miR-10a-5p specific oligonucleotide probe and/or forming a complex between one or more miR-10b-5p fragments and a miR-10b-5p specific oligonucleotide probe to provide a miR-10a-5p and/or miR-10b-5p blocked sample;
preparing a library using the miR-10a-5p and/or miR-10b-5p blocked sample; and
sequencing the library.

In one embodiment, the 5'end, the 3'end or both ends of each miR-10a-5p specific oligonucleotide probe and/or miR-10b-5p specific oligonucleotide probe is modified to prevent ligation.

In a further embodiment, the 5'end or the 3'end of each miR-10a-5p specific oligonucleotide probe and/or miR-10b-5p specific oligonucleotide probe is modified by incorporating a dideoxy nucleotide.

In a further embodiment, the 5'end or the 3'end of each miR-10a-5p specific oligonucleotide probe and/or miR-10b-5p specific oligonucleotide probe is modified with biotin.

In a further embodiment, the 5'end of each miR-10a-5p specific oligonucleotide probe and/or miR-10b-5p specific oligonucleotide probe is modified with biotin and the 3'end of each miR-10a-5p specific oligonucleotide probe and/or miR-10b-5p specific oligonucleotide probe is modified by incorporating a dideoxy nucleotide.

In a further aspect, disclosed are kits that are useful for improving global gene expression analysis for a population of RNA molecules derived from human urine. The kit comprises one or more miR-10a-5p specific oligonucleotide probes, wherein each miR-10a-5p specific oligonucleotide probe comprises a nucleotide sequence that is the complement to a nucleotide sequence of miR-10a-5p and/or, one or more miR-10b-5p specific oligonucleotide probes, wherein each miR-10b-5p specific oligonucleotide probe comprises a nucleotide sequence that is the complement to a nucleotide sequence of miR-10b-5p.

In one embodiment, the 5'end, the 3'end or both ends of each miR-10a-5p specific oligonucleotide probe and/or miR-10b-5p specific oligonucleotide probe is modified.

In a further embodiment, the 5'end or the 3'end of each miR-10a-5p specific oligonucleotide probe and/or miR-10b-5p specific oligonucleotide probe is modified with biotin.

In a further embodiment, the 5'end or the 3'end of each miR-10a-5p specific oligonucleotide probe and/or miR-10b-5p specific oligonucleotide probe is modified with digoxigenin.

In a further embodiment, the 5'end of each miR-10a-5p specific oligonucleotide probe and/or miR-10b-5p specific oligonucleotide probe is modified with dinitrophenol.

In a further embodiment, the 3'end of each miR-10a-5p specific oligonucleotide probe and/or miR-10b-5p specific oligonucleotide probe is modified by incorporating a dideoxy nucleotide.

In a further embodiment, the 5'end of each miR-10a-5p specific oligonucleotide probe and/or miR-10b-5p specific oligonucleotide probe is modified with biotin and the 3'end of each miR-10a-5p specific oligonucleotide probe and/or miR-10b-5p specific oligonucleotide probe is modified by incorporating a dideoxy nucleotide.

In a further embodiment, the miR-10a-5p specific oligonucleotide probe and/or miR-10b-5p specific oligonucleotide probe is immobilized on a solid support.

In an embodiment of any of the methods or kits described above, the nucleotide sequence of miR-10a-5p has at least 90% sequence identity to the nucleotide sequence of SEQ ID NO: 1. In a further embodiment, the nucleotide sequence of miR-10a-5p comprises the nucleotide sequence of SEQ ID NO: 1.

In another embodiment of any of the methods or kits described above, the nucleotide sequence of miR-10b-5p has at least 90% sequence identity to the nucleotide sequence of SEQ ID NO: 3. In a further embodiment, the nucleotide sequence of miR-10b-5p comprises the nucleotide sequence of SEQ ID NO: 3.

In another embodiment of any of the methods or kits described above, the miR-10a-5p specific oligonucleotide probe has at least 90% sequence identity to the nucleotide sequence of SEQ ID NO: 2. In a further embodiment, the miR-10a-5p specific oligonucleotide probe comprises the nucleotide sequence of SEQ ID NO: 2.

In another embodiment of any of the methods or kits described above, the miR-10b-5p specific oligonucleotide probe has at least 90% sequence identity to the nucleotide sequence of SEQ ID NO: 4. In a further embodiment, the miR-10b-5p specific oligonucleotide probe comprises the nucleotide sequence of SEQ ID NO: 4.

DESCRIPTION

Figure 1:
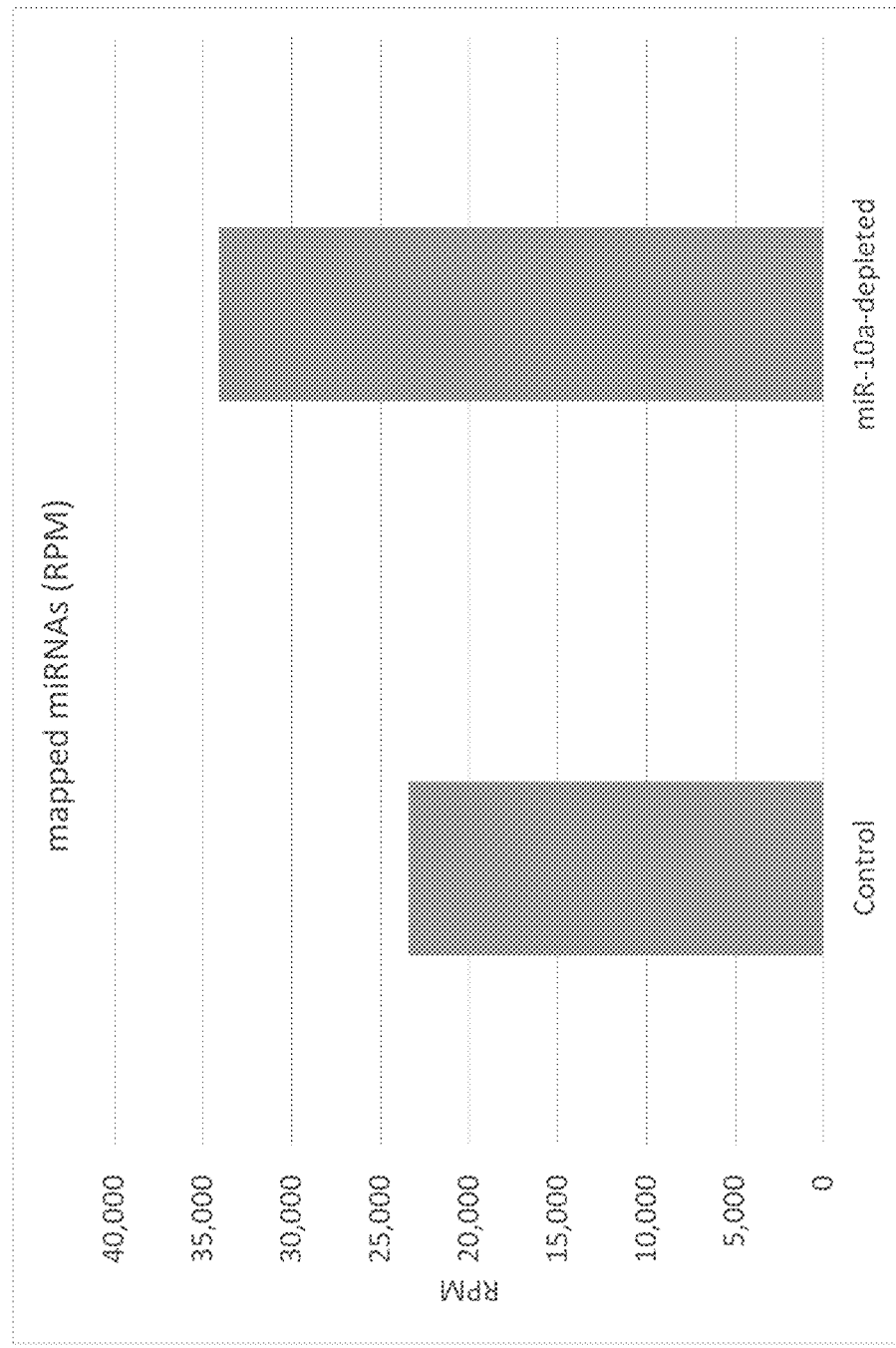
FIG. 1 is a graph that shows the number of read per million (RPM) mapped miRNAs over all clipped reads for a control (non-depleted) urine RNA sample and miR-10a-5p fragment-depleted urine RNA samples from healthy donors.

It has now been demonstrated that the disproportionate abundance of miR-10a-5p and miR-10b-5p fragments in human urine RNA samples poses a major impediment to accurate detection and quantification of other, better characterized and/or more diagnostically relevant miRNAs. The challenges experienced in the generation of a global expression profile of miRNA in urine—due to the sheer amount of miR-10a-5p and miR-10b-5p present in human urine—are well exemplified in global gene expression analysis employing next generation sequencing (NGS).

There are many different platforms that can be used for NGS of small RNA, including Roche 454, Roche GS FLX Titanium, Illumina MiSeq, Illumina HiSeq, Illumina Genome Analyzer IIX, Illumina MiniSeq, Illumina NextSeq, Illumina NovaSeq Life Technologies SOLiD4, Life Technologies Ion Proton, Complete Genomics, Helicos Biosciences Heliscope, and Pacific Biosciences SMRT. All of these different platforms follow the same general procedure for NGS of small RNA. Namely, a DNA sequencing library is prepared using purified RNA. Library preparation includes transcribing the RNA into cDNA, ligating the cDNA molecules with 5' and 3' adaptors, and amplifying the ligated DNA fragments. These relatively short DNA fragments are then massively parallel sequenced and bioinformatics analysis applied to de-multiplex samples, align, annotate and aggregate reads.

Within the total population of miRNAs present in human urine, it has been found that certain miRNAs are disproportionately abundant. Two of the most overrepresented miRNAs are miR-10a-5p and miR-10b-5p, which can account for over 50% of the miRNA present in in human urine (El-Mogy et al., 2018). These miRNAs have been extensively studied in many biological pathways, including cancer development and progression (Veerla et al., 2009; Xiao et al., 2014; Ma et al., 2015; Zhang et al., 2015; Abdelmaksoud-Dammak et al., 2017; Arai et al., 2017). It has now been demonstrated that the disproportionate abundance of miR-10a-5p and miR-10b-5p in human urine RNA samples poses a major impediment to accurate detection and quantification of other, less abundant and/or potentially predictive miRNAs. The challenges experienced in the generation of a global expression profile of miRNA in urine—due to the sheer amount of miR-10a-5p and miR-10b-5p present in the miRNA found in human urine—are well exemplified in global gene expression analysis employing NGS.

The number of times each sequence in the library has been "read" (e.g. sequenced) is of utmost importance in determining both how reliably it can be called and its abundance relative to other sequences in the same sample. As miR-10a-5p and miR-10b-5p are of the most abundant miRNA sequences in human urine, the greatest proportion of miRNA reads in any given small RNA library—prepared from RNA purified from human urine—is mapped to these two miRNAs (Zhou et al., 2017). In the case of global miRNA expression analysis, this produces much less reliable data for relatively rare miRNA transcripts, which may be read at the level of "noise", or not called at all, because they constitute a very small proportion of miRNAs at the outset. The total number of all reads for any sample on any NGS platform is finite. As such, a much smaller proportion of reads is allocated for all the other miRNAs present, which may be of a much greater interest than miR-10a-5p and miR-10b-5p. The sequencing of the library will be skewed towards the sequencing of these overly abundant miR-10a-5p and miR-10b-5p fragments.

It has now been surprisingly found that global gene expression analysis for small RNA samples derived from human urine samples can be improved by selectively depleting the abundant miR-10a-5p and/or miR-10b-5p fragments prior to library preparation or by selectively blocking the miR-10a-5p and/or miR-10b-5p fragments in the RNA samples to prevent them from acting as a substrate during library preparation. By selectively depleting or blocking the miR-10a-5p and/or miR-10b-5p fragments, it is possible to improve the ratio of useful data (e.g. data mapped to less abundant miRNAs of interest) to non-useful data (e.g. data mapped to miR-10a-5p or miR-10b-5p fragments). As a result, global gene expression analysis can be improved, for example, by increasing the sensitivity of the global gene expression analysis (e.g. reduction of background noise) and by increasing the reliability of the obtained expression data. This can be beneficial when performing research and discovery of novel miRNA markers in human urine, as well as studies that rely on the ability to see changes in low expressing but significant miRNA.

Method of Improving Global Gene Expression Analysis of Human Urine Derived RNA

Disclosed is a method of improving global gene expression analysis for a population of RNA molecules derived from human urine.

As used herein, "global gene expression analysis" includes any quantitative method for investigating a population of RNA species. In the disclosed method, the population of RNA species are derived from human urine. Global gene expression analysis can be carried out, for example, by way of microarray analysis, library construction, reverse transcription, amplification, transcriptome profiling, expression analysis and sequencing, including next generation sequencing.

Selectively depleting or blocking miR-10a-5p and/or miR-10b-5p fragments present in the population of RNA molecules can improve global gene expression analysis in a population of RNA molecules derived from human urine. By selectively depleting or blocking the miR-10a-5p and/or miR-10b-5p fragments present in the population of RNA molecules, the ratio of useful data (e.g. data mapped to miRNAs of interest) to non-useful data (e.g. data mapped to miR-10a-5p or miR-10b-5p fragments) obtained by the global gene expression analysis is improved.

One embodiment of the disclosed method of improving global gene expression analysis for a population of RNA molecules derived from human urine comprises selectively depleting or blocking miR-10a-5p fragments present in the population of RNA molecules. In another embodiment, the method comprises selectively depleting or blocking miR-10b-5p fragments present in the population of RNA molecules. In a further embodiment, the method comprises selectively depleting or blocking miR-10a-5p fragments and miR-10b-5p fragments present in the population of RNA molecules.

Human Urine Derived RNA Molecules

The disclosed method for improving global gene expression can be performed using an initial population of RNA molecules, which is total RNA isolated from human urine. Urine samples can be collected and stored using conventional methods known in the art. It may be desirable to employ urine collection tubes that prevent RNA degradation, such as, but not limited to Norgen's Urine Collection and Preservation Tubes (Cat #18116, 18120, 18111, Norgen Biotek Corp., Thorold, Canada). Methods for the isolation of total RNA from human urine are well known in the art. Suitable methods for the isolation of total RNA include but are not limited to the use of phenol/chloroform, the use of silicon carbide (SiC), the use of silica, and alcohol precipitation.

The initial population of RNA molecules can also be small RNA isolated from human urine. Again, suitable methods for the isolation of small RNA are known in the art. Suitable methods include, but are not limited to, the use of phenol/chloroform, the use of silicon carbide, and the use of silica. In a preferred embodiment, the initial population of RNA molecules is small RNA isolated from human urine samples using SiC.

Selective Depletion of miR-10a-5p and/or miR-10b-5p Fragments

In one embodiment, disclosed is a method of improving global gene expression analysis for a population of RNA molecules derived from human urine, wherein the method comprises the step of depleting miR-10a-5p fragments from the population of RNA molecules. It will be appreciated that the disclosed method does not require the complete removal of all miR-10a-5p fragments.

The resulting population of RNA molecules that are depleted of miR-10a-5p fragments can be used in downstream global gene expression analysis applications. This method is particularly suitable for preparing small RNA for next generation sequencing applications. By removing the highly abundant miR-10a-5p fragments prior to preparation of the sequencing library, the signal to noise ratio can be improved.

miR-10a-5p fragments can be depleted from the population of RNA molecules by selectively removing the fragments. In one embodiment, miR-10a-5p fragments are selectively removed by:

adding miR-10a-5p specific oligonucleotide probes to a sample containing the population of RNA molecules, wherein each miR-10a-5p specific oligonucleotide probe comprises a nucleotide sequence that is the complement to a nucleotide sequence of miR-10a-5p;

forming a complex between one or more miR-10a-5p fragments and a miR-10a-5p specific oligonucleotide probe; and removing the miR-10a-5p:oligonucleotide complexes from the sample.

The miR-10a-5p specific oligonucleotide probes are designed to be complementary to miR-10a-5p, and thus are capable of hybridizing with the miR-10a-5p fragments. The miR-10a-5p specific oligonucleotide probe can be various lengths, so long as it contains sufficient bases to allow the probe to specifically bind to the miR-10a-5p fragments. The miR-10a-5p specific oligonucleotide probe may be 6-200 bases and more preferably 20-50 bases.

In a more preferred embodiment, the miR-10a-5p specific oligonucleotide probe is designed to be the complement of the 23 base miR-10a-5p fragment with the sequence:

(SEQ ID NO: 1)
5'-UACCCUGUAGAUCCGAAUUUGUG-3'.

In this embodiment, the miR-10a-5p specific oligonucleotide probe can comprise the following sequence:

(SEQ ID NO: 2)
5'-CACAAATTCGGATCTACAGGGTA-3'.

In further preferred embodiments, the miR-10a-5p specific oligonucleotide probe can be designed to be the complement of a nucleotide having at least 90%, 95% or 99% identity with the nucleotide sequence of SEQ ID NO:1. The miR-10a-5p specific oligonucleotide probe can comprise a nucleotide sequence having at least 90%, 95% or 99% identity with the nucleotide sequence of SEQ ID NO:2.

In a further embodiment, the miR-10a-5p specific oligonucleotide probe may comprise one or multiple copies of the complement to the miR-10a-5p fragment. The miR-10a-5p specific oligonucleotide probe may comprise 2-20 copies of the complement to the miR-10a-5p fragment, and more preferably comprises 7 copies of the complement to the miR-10a-5p fragment.

After hybridization, the miR-10a-5p:oligonucleotide complexes are removed from the RNA sample to provide the miR-10a-5p depleted population of RNA molecules. A variety of different methods can be employed to remove the miR-10a-5p:oligonucleotide complexes from the RNA sample.

In one embodiment, the miR-10a-5p specific oligonucleotide probe includes modifications to facilitate the use of solid supports for the selective removal of the miR-10a-5p:oligonucleotide complexes. For example, the miR-10a-5p specific oligonucleotide probe may include a 5'end modification, a 3'end modification, an internal modification or combination thereof, that allows the miR-10a-5p:oligonucleotide complexes to covalently or non-covalently bind to a solid support, which comprises a functional group, a protein or an antibody, which specifically interacts with the modification. For example, the oligonucleotide probe can be provided with a 5' or 3' biotin modification for selective binding to solid supports comprising avidin or streptavidin. The oligonucleotide probe can be provided with a 5' or 3' digoxigenin modification for selective binding to solid supports comprising digoxigenin specific antibodies. The oligonucleotide probe can be provided with a 5' dinitrophenol modification for selective binding to solid supports comprising dinitrophenol specific antibodies. Examples of solid supports that may be used to selectively remove miR-10a-5p:oligonucleotide complexes include resin packed columns and purification beads, which may be magnetic or non-magnetic (such as polystyrene).

In a preferred embodiment, the miR-10a-5p:oligonucleotide complexes are removed by:

selectively binding the miR-10a-5p:oligonucleotide complexes to a solid support comprising a protein or antibody that specifically interacts with an end modification on the oligonucleotide probe; and collecting an unbound fraction of the sample containing the miR-10a-5p depleted population of small RNA molecules.

The miR-10a-5p specific oligonucleotide probe preferably comprises a 5'end or a 3'end biotin modification and the solid support preferably comprises magnetic beads that are coupled to avidin or streptavidin. In a further preferred embodiment, the magnetic beads are coupled to streptavidin. Following selectively binding of the miR-10a-5p:oligonucleotide complexes to the magnetic beads, the bound magnetic beads can be removed from the RNA sample using a magnet, thereby removing the miR-10a-5p:oligonucleotide complex from the RNA sample. The unbound fraction of RNA sample containing the miR-10a-5p depleted population of small RNA molecules can then be collected for use in downstream global gene expression analysis applications.

In another embodiment, the miR-10a-5p specific oligonucleotide probes can be immobilized onto a solid support. In this embodiment, the RNA sample containing the population of RNA molecules can be added to the solid support or vice versa. miR-10a-5p fragments will hybridize to the oligonucleotide probes immobilized on the solid support. The unbound fraction of the sample containing the miR-10a-5p depleted population of small RNA molecules can then be collected for use in downstream global gene expression analysis applications.

In another embodiment, the miR-10a-5p:oligonucleotide complexes can be removed from the RNA sample using size exclusion chromatography, which is based on the differential binding of molecules to a matrix based on size. In a preferred embodiment, silica columns can be used to separate the miR-10a-5p:oligonucleotide complexes from the mixture.

In a further embodiment, the miR-10a-5p:oligonucleotide complexes can be removed from the RNA sample using a size selective isolation method employing SiC. The RNA sample containing the miR-10a-5p:oligonucleotide complexes can be combined with a binding buffer, an alcohol and SiC to provide a binding mixture. The alcohol concentration of the binding mixture is adjusted to determine the cut-off size of RNA molecules that will be preferentially bound to the SiC. By using a lower alcohol concentration, the larger miR-10a-5p:oligonucleotide complexes contained in the RNA sample will selectively bind to the SiC, whereas the smaller miRNAs will remain in the liquid phase.

The alcohol concentration in the binding mixture can be adjusted using any alcohol known in the art. Examples of suitable alcohols include are but not limited to ethanol, isopropanol and methanol. To achieve size selective binding of the miR-10a-5p:oligonucleotide complexes to the SiC, the alcohol concentration of the binding mixture can preferably be adjusted with ethanol to a concentration of between 1-30% (v/v), and more preferably between 1-10% (v/v).

The size selective isolation method can be performed using a SiC slurry or a SiC column. In either embodiment, the size selective binding step can be performed under low salt conditions and slightly acidic to neutral pH conditions of about pH 4-7. The larger miR-10a-5p:oligonucleotide complexes contained in the RNA sample will come into contact with the SiC and selectively bind to the SiC particles. The unbound small miRNAs will remain in the liquid phase. In embodiments employing SiC in a slurry format, the liquid phase containing the small miRNAs can be collected, for example, by pelleting the SiC through centrifugation and decanting the liquid phase containing the small miRNAs. For embodiments using a SiC column, such as a spin column, the larger miR-10a-5p:oligonucleotide complexes selectively bound to the SiC will be retained in the column and the flowthrough collected. The collected small miRNAs can be used in downstream global gene expression analysis.

In a further embodiment, disclosed is a method of improving global gene expression analysis for a population of RNA molecules derived from human urine, wherein the method comprises the step of depleting miR-10b-5p fragments from the population of RNA molecules. It will be appreciated that the disclosed method does not require the complete removal of all miR-10b-5p fragments The miR-10b-5p fragments can be depleted from the population of RNA molecules by selectively removing the fragments. In one embodiment, miR-10b-5p fragments are selectively removed by:

adding miR-10b-5p specific oligonucleotide probes to a sample containing the population of RNA molecules, wherein each probe comprises a nucleotide sequence that is the complement to the nucleotide sequence of miR-10b-5p;

forming a complex between one or more miR-10b-5p fragments and a miR-10b-5p specific oligonucleotide probe; and removing the miR-10b-5p:oligonucleotide complexes from the sample.

The miR-10b-5p specific oligonucleotide probe can be various lengths, so long as it contains sufficient bases to allow the probe to specifically bind to the miR-10b-5p fragments. The oligonucleotide probe may be 6-200 bases and more preferably 20-50 bases.

In a more preferred embodiment, the oligonucleotide probe is designed to be the complement of the 23 base miR-10b-5p fragment having the sequence:

(SEQ ID NO: 3)
5'-UACCCUGUAGAACCGAAUUUGUG-3'.

In this embodiment, the oligonucleotide probe can comprise the following sequence:

(SEQ ID NO: 4)
5'-CACAAATTCGGTTCTACAGGGTA-3'.

In further preferred embodiments, the miR-10b-5p specific oligonucleotide probe can be designed to be the complement of a nucleotide having at least 90%, 95% or 99% identity with the nucleotide sequence of SEQ ID NO:3. The miR-10b-5p specific oligonucleotide probe can comprise a nucleotide sequence having at least 90%, 95% or 99% identity with the nucleotide sequence of SEQ ID NO:4.

In a further embodiment, the oligonucleotide probe may comprise one or multiple copies of the complement to the miR-10b-5p fragment. The miR-10b-5p specific oligonucleotide probe may comprise 2-20 copies of the complement to the miR-10b-5p fragment, and more preferably comprises 7 copies of the complement to the miR-10b-5p fragment.

After hybridization, the miR-10b-5p:oligonucleotide complexes are removed from the RNA sample to provide the miR-10b-5p depleted population of RNA molecules. A variety of different methods can be employed to remove the miR-10b-5p:oligonucleotide complexes from the RNA sample including selective binding to a solid support and size selective isolation using a SiC slurry or a SiC column as described above. It will be apparent to the skilled person that the methods described herein for the removal of miR-10a-5p:oligonucleotide complexes can be adapted for the removal of miR-10b-5p:oligonucleotide complexes, for example, through the use of modified miR-10b-5p specific oligonucleotide probes.

The disclosed method of improving global gene expression analysis for a population of RNA molecules derived from human urine may comprise the selective depletion of miR-10a-5p fragments or the selective depletion miR-10b-5p fragments. In alternate embodiments, the method may comprise the selective depletion of miR-10a-5p fragments and miR-10b-5p fragments, wherein the step of depleting the miR-10a-5p fragments and the step of depleting the miR-10b-5p fragments are carried out successively or concurrently.

Selective Blocking of miR-10a-5p and/or miR-10b-5p Fragments

In another embodiment, disclosed is a method of improving global gene expression analysis for a population of RNA molecules derived from human urine, wherein the method comprises the step of selectively blocking miR-10a-5p fragments in the population of RNA molecules.

As used herein, "selectively blocking miR-10a-5p fragments" refers to any modification that renders the miR-10a-5p fragments an unsuitable substrate in a downstream global gene expression analysis application. For example, the miR-10a-5p fragments can be blocked by hybridizing the miR-10a-5p fragments with a miR-10a-5p specific oligonucleotide probe having a complementary sequence to form miR-10a-5p:oligonucleotide complexes.

The resulting population of RNA molecules including the blocked miR-10a-5p fragments can be used in downstream global gene expression analysis applications. This method is particularly suitable for preparing small RNA for next generation sequencing applications in order to improve the signal to noise ratio. By blocking the highly abundant miR-10a-5p fragments (e.g. by forming double stranded DNA-RNA hybrids with the miR-10a-5p specific oligonucleotide probes), these fragments will no longer be a suitable substrate for any of the steps in library preparation, including the initial attachment of the 5' and 3' adaptors.

The miR-10a-5p fragments can be selectively blocked in a population of RNA molecules by:
  adding miR-10a-5p specific oligonucleotide probes to a sample containing the population of RNA molecules, wherein each miR-10a-5p specific oligonucleotide probe comprises a nucleotide sequence that is the complement to a nucleotide sequence of miR-10a-5p; and
  forming a complex between one or more miR-10a-5p fragments and a miR-10a-5p specific oligonucleotide probe.

Any of the miR-10a-5p specific oligonucleotide probes described above can be used to selectively block the miR-10a-5p fragments contained in the RNA sample by forming a complex between the miR-10a-5p fragments and the miR-10a-5p specific oligonucleotide probe.

In a further embodiment, the 5'end, the 3'end or both ends of the miR-10a-5p specific oligonucleotide probe is modified to prevent ligation. The 5'end of the miR-10a-5p specific oligonucleotide probe can be selectively blocked through the use of inverted dideoxy-T, the use of dephoshorylated 5' ends, the use of biotin and any other suitable 5'end modification method. The 3' end of the miR-10a-5p specific oligonucleotide probe can also be blocked using a suitable 3'end modification method, including but not limited to, the use of inverted dT, dideoxy-C, and other dideoxy nucleotides.

In a preferred embodiment, the miR-10a-5p specific oligonucleotide probe is blocked at both the 5' and 3' end, thereby preventing the attachment of 5' and 3' adaptors to the miR-10a-5p specific oligonucleotide probe. By blocking one or both ends of the miR-10a-5p specific oligonucleotide probe, it is possible to avoid the miR-10a-5p specific oligonucleotide probes themselves being incorporated into the sequence library and contributing to the background noise. In a preferred embodiment, the miR-10a-5p specific oligonucleotide probe is blocked using a biotin at the 5' end and using a dideoxy base at the 3' end.

In another embodiment, disclosed is a method of improving global gene expression analysis for a population of RNA molecules derived from human urine, wherein the method comprises the step of selectively blocking miR-10b-5p fragments in the population of RNA molecules.

As used herein, "selectively blocking miR-10b-5p fragments" refers to any modification that renders the miR-10b-5p fragments an unsuitable substrate in a downstream global gene expression analysis application. For example, the miR-10b-5p fragments can be blocked by hybridizing the miR-10b-5p fragments with a miR-10b-5p specific oligonucleotide probe having a complementary sequence to form miR-10b-5p:oligonucleotide complexes.

The resulting population of RNA molecules including the blocked miR-10b-5p fragments can also be used in downstream global gene expression analysis applications. This method is also particularly suitable for preparing small RNA for next generation sequencing applications in order to improve the signal to noise ratio. By blocking the highly abundant miR-10b-5p fragments (e.g. by forming double stranded DNA-RNA hybrids with the miR-10b-5p specific oligonucleotide probes), these fragments will no longer be a suitable substrate for any of the steps in library preparation, including the initial attachment of the 5' and 3' adaptors.

The miR-10b-5p fragments can be selectively blocked in a population of RNA molecules by:
  adding miR-10b-5p specific oligonucleotide probes to a sample containing the population of RNA molecules, wherein each miR-10b-5p specific oligonucleotide probe comprises a nucleotide sequence that is the complement to a nucleotide sequence of miR-10b-5p; and
  forming a complex between one or more miR-10b-5p fragments and a miR-10b-5p specific oligonucleotide probe.

Any of the miR-10b-5p specific oligonucleotide probes described above can be used to selectively block the miR-10b-5p fragments contained in the RNA sample by forming a complex between the miR-10b-5p fragments and the miR-10b-5p specific oligonucleotide probe.

In a further embodiment, the 5'end, the 3'end or both ends of the miR-10b-5p specific oligonucleotide probe are modified to prevent ligation. The miR-10b-5p specific oligonucleotide probe can be similarly modified as described above for modified miR-10a-5p specific oligonucleotide probes.

The disclosed method may comprise selectively blocking of miR-10a-5p fragments or selectively blocking miR-10b-5p fragments. In alternate embodiments, the method may comprise selectively blocking of miR-10a-5p fragments and miR-10b-5p fragments, wherein the step of blocking miR-10a-5p fragments and the step of blocking miR-10b-5p fragments are carried out successively or concurrently.

Next Generation Sequencing and Small RNA Libraries

Further disclosed is a method of performing next generation sequencing of a population of small RNA derived from human urine. In one embodiment, the method comprises the provision of a miR-10a-5p fragment depleted population of small RNA molecules, which is then used to prepare the sequencing library. By removing the highly abundant miR-10a-5p fragments prior to the preparation of the sequencing library, the sequencing capacity for the less abundant small RNA species is increased and the efficiency of the sequencing reaction improved. Fewer resources are wasted during both the library preparation and sequencing steps since the depleted miR-10a-5p fragments will not form part of the sequencing library and will therefore not be read during the sequencing.

In a preferred embodiment, the method of performing next generation sequencing of a population of small RNA derived from human urine comprises:
  adding miR-10a-5p specific oligonucleotide probes to a sample containing the population of RNA molecules, wherein each probe comprises a nucleotide sequence that is the complement to a nucleotide sequence of miR-10a-5p;
  forming a complex between one or more miR-10a-5p fragments and a miR-10a-5p specific oligonucleotide probe; and
  removing the miR-10a-5p:oligonucleotide complexes from the sample, wherein the remaining sample contains a miR-10a-5p depleted population of small RNA molecules;
  preparing a library using the remaining sample; and
  sequencing the library.

The miR-10a-5p depletion steps can be performed as described in greater detail above. The library preparation steps and sequencing steps can be performed in accordance with known NGS protocols.

In another embodiment, the method of performing next generation sequencing of a population of small RNA derived from human urine comprises blocking the miR-10a-5p fragments contained in the population of RNA molecules to be sequenced, prior to the preparation of the library. By blocking the miR-10a-5p fragments before the library is generated, the sequencing capacity for the less abundant small RNA species is increased and the efficiency of the sequencing reaction improved. Fewer resources are wasted during both the library preparation and sequencing steps since the blocked miR-10a-5p fragments will not act as a substrate during the library preparation and will therefore not be read during the sequencing. Further, by using 5'end and/or 3'end modified miR-10a-5p specific oligonucleotide probes which are themselves blocked, incorporation of the oligonucleotide probes into the sequence library and the consequential increase in background noise can be avoided.

In a preferred embodiment, disclosed is a method of performing next generation sequencing of small RNA from a sample, comprising:
  adding miR-10a-5p specific oligonucleotide probes to a sample containing the population of RNA molecules, wherein each miR-10a-5p specific oligonucleotide probe comprises a nucleotide sequence that is the complement to a nucleotide sequence of miR-10a-5p; and
  forming a complex between one or more miR-10a-5p fragments and a miR-10a-5p specific oligonucleotide probe to provide a miR-10a-5p blocked sample;
  preparing a library using the miR-10a-5p blocked sample; and
  sequencing the library.

The miR-10a-5p blocking steps can be performed as described in greater detail above. In a further embodiment, the miR-10a-5p specific oligonucleotide probe can be modified at the 5'end, the 3' end or at both ends as described above in greater detail.

The library preparation steps and sequencing steps can be performed in accordance with known NGS protocols.

In another embodiment, the method comprises the provision of a miR-10b-5p fragment depleted population of small RNA molecules, which is then used to prepare the sequencing library. By removing the highly abundant miR-10b-5p fragments prior to the preparation of the sequencing library, the sequencing capacity for the less abundant small RNA species is increased and the efficiency of the sequencing reaction improved. Fewer resources are wasted during both the library preparation and sequencing steps since the depleted miR-10b-5p fragments will not form part of the sequencing library and will therefore not be read during the sequencing.

In a preferred embodiment, the method of performing next generation sequencing of a population of small RNA derived from human urine comprises:
  adding miR-10b-5p specific oligonucleotide probes to a sample containing the population of RNA molecules, wherein each probe comprises a nucleotide sequence that is the complement to a nucleotide sequence of miR-10b-5p;
  forming a complex between one or more miR-10b-5p fragments and a miR-10b-5p specific oligonucleotide probe; and
  removing the miR-10b-5p:oligonucleotide complexes from the sample, wherein the remaining sample contains a miR-10b-5p depleted population of small RNA molecules;
  preparing a library using the remaining sample; and
  sequencing the library.

The miR-10b-5p depletion steps can be performed as described in greater detail above. The library preparation steps and sequencing steps can be performed in accordance with known NGS protocols.

In another embodiment, the method of performing next generation sequencing of a population of small RNA derived from human urine comprises blocking the miR-10b-5p fragments contained in the population of RNA molecules to be sequence, prior to the preparation of the library. By blocking the miR-10b-5p fragments before the library is generated, the sequencing capacity for the less abundant small RNA species is increased and the efficiency of the sequencing reaction improved. Fewer resources are wasted during both the library preparation and sequencing steps since the blocked miR-10b-5p fragments will not act as a substrate during the library preparation and will therefore not be read during the sequencing. Further, by using 5'end and/or 3'end modified oligonucleotide probes which are themselves blocked, incorporation of the oligonucleotide probes into the sequence library and the consequential increase in background noise can be avoided.

In another embodiment, disclosed is a method of performing next generation sequencing of small RNA from a sample, comprising:
  adding miR-10b-5p specific oligonucleotide probes to a sample containing the population of RNA molecules, wherein each miR-10b-5p specific oligonucleotide probe comprises a nucleotide sequence that is the complement to a nucleotide sequence of miR-10b-5p; and
  forming a complex between one or more miR-10b-5p fragments and a miR-10b-5p specific oligonucleotide probe to provide a miR-10b-5p blocked sample;

preparing a library using the miR-10b-5p blocked sample; and sequencing the library.

The miR-10b-5p blocking steps can be performed as described in greater detail above. In a further embodiment, the miR-10b-5p specific oligonucleotide probe can be modified at the 5'end, the 3' end or both ends. The miR-10b-5p specific oligonucleotide probe can be similarly modified as described above for modified miR-10a-5p specific oligonucleotide probes.

The library preparation steps and sequencing steps can be performed in accordance with known NGS protocols.

In one embodiment, the disclosed method of performing next generation sequencing may comprise the preparation of a library using a miR-10a-5p depleted population of small RNA molecules or a miR-10b-5p depleted population of small RNA molecules. In an alternate embodiment, the method may comprise the preparation of a library using a miR-10a-5p and miR-10b-5p depleted population of small RNA molecules, wherein the steps of depleting the miR-10a-5p fragments and the miR-10b-5p fragments are carried out successively or concurrently.

In another embodiment, the disclosed method of performing next generation sequencing may comprise the preparation of a library using a miR-10a-5p blocked sample or a miR-10b-5p blocked sample. In an alternate embodiment, the method may comprise the preparation of a library using a miR-10a-5p blocked and a miR-10b-5p blocked sample, wherein the steps of selectively blocking the miR-10a-5p fragments and the miR-10b-5p fragments are carried out successively or concurrently.

Kits for Improving Global Gene Expression Analysis

Further disclosed, is a kit for improving global gene expression analysis for a population of RNA molecules derived from human urine. The kit can comprise one or more miR-10a-5p specific oligonucleotide probes, wherein each miR-10a-5p specific oligonucleotide probe comprises a nucleotide sequence that is the complement to a nucleotide sequence of miR-10a-5p and/or one or more miR-10b-5p specific oligonucleotide probes, wherein each miR-10b-5p specific oligonucleotide probe comprises a nucleotide sequence that is the complement to a nucleotide sequence of miR-10b-5p.

The kit may comprise any of the miR-10a-5p specific oligonucleotide probes described in greater detail above. The miR-10a-5p specific oligonucleotide probes can be used to block the miR-10a-5p fragments by forming miR-10a-5p:oligonucleotide complexes. In a preferred embodiment, such miR-10a-5p specific oligonucleotide probes include a 5'end and/or 3'end modification to prevent ligation of the probes. For example, the 5'end or the 3'end can be modified by incorporating a dideoxy nucleotide as described in greater detail above.

Alternatively, the miR-10a-5p specific oligonucleotide probes can be used to form miR-10a-5p:oligonucleotide complexes, which are subsequently removed from the population of RNA molecules. The miR-10a-5p specific oligonucleotide probes may include a modification to facilitate removal of the miR-10a-5p:oligonucleotide complex from a sample using a solid support. For example, the 5'end or the 3'end of the oligonucleotide probe can be modified with biotin for use with avidin or streptavidin coupled solid supports. Further examples of suitable modifications for use with solid supports are described in greater detail above.

The kit may comprise any of the miR-10b-5p specific oligonucleotide probes described in greater detail above. The miR-10b-5p specific oligonucleotide probes can be used to block the miR-10b-5p fragments by forming miR-10b-5p:oligonucleotide complexes. In a preferred embodiment, such miR-10b-5p specific oligonucleotide probes include a 5'end and/or 3'end modification to prevent ligation of the probes. For example, the 5'end or the 3'end can be modified by incorporating a dideoxy nucleotide as described in greater detail above. The same modifications described above for miR-10a-5p specific oligonucleotide probes can also be incorporated into miR-10b-5p specific oligonucleotide probes.

The miR-10b-5p specific oligonucleotide probes can also be used to form miR-10b-5p:oligonucleotide complexes, which are subsequently removed from the population of RNA molecules. The miR-10b-5p specific oligonucleotide probes may include a modification to facilitate removal of the miR-10b-5p:oligonucleotide complex from a sample using a solid support. For example, the 5'end or the 3'end of the miR-10b-5p specific oligonucleotide probe can be modified with biotin for use with avidin or streptavidin coupled solid supports. Further examples of suitable modifications for use with solid supports are described in greater detail above. The same modifications described above for miR-10a-5p specific oligonucleotide probes can also be incorporated into miR-10b-5p specific oligonucleotide probes.

In another embodiment, the miR-10a-5p specific oligonucleotide probes and/or the miR-10b-5p specific oligonucleotide probes can be provided immobilized on a solid support, such as purification beads, which may be magnetic or non-magnetic.

The kit may be designed for use in the selective depletion, selective blocking, sequencing and library generation methods as described above and may comprise further components. Each component may be provided in separate compartments or vessels. The kit may also be provided with instructions for using the kit, or with directions for how instructions may be obtained.

Although the invention has been described with reference to illustrative embodiments, it is to be understood that the invention is not limited to these precise embodiments, and that various changes and modification are to be intended to be encompassed in the appended claims.

EXAMPLES

These examples are described for the purposes of illustration and are not intended to limit the scope of the invention.

Example 1—Preparation of Capture Probe for miR-10a-5p Fragment

The capture probe for the miR-10a-5p fragment was designed by using the "*Homo sapiens* miRNA 10a" (miRBase accession: MIMAT0000253) as a reference sequence for the full length miR-10a-5p and creating a complement of the 23 nucleotides in the sequence. This was based on previous observations and sequencing data of small RNA purified from human urine, which showed that the second most over-represented sequence in the small RNA fraction of RNA purified from urine was the 23 nucleotides long miR-10a-5p (El-Mogy et al., 2018).

The capture probe was designed to be the complement of the 23 base miR-10a-5p fragment having the sequence

5'-UACCCUGUAGAUCCGAAUUUGUG-3'. (SEQ ID NO: 1)

The sequence of the oligonucleotide capture probe is:

5'-CACAAATTCGGATCTACAGGGTA-3'. (SEQ ID NO: 2)

In order to facilitate the removal of the miR-10a-5p: capture oligonucleotide complexes, biotin was covalently attached to the 5' end of the capture oligonucleotide.

Example 2—Depletion of the miR-10a-5p Fragment from Human Urine

A 30 mL urine sample was collected into a 50 cc Falcon tube (BD Diagnostics, Mississauga, Canada) from 6 healthy donors (3 males and 3 females). Total RNA was then purified from the 30 mL of the human urine using Norgen's Urine Cell-Free Circulating RNA Purification Maxi Kit (Cat #57100, Norgen Biotek Corp., Thorold, Canada) according to the provided protocol.

Next, the miR-10a-5p fragment was depleted from the total RNA sample using the probe described in Example 1. Briefly, Streptavidin Magnetic Beads were prepared by aliquoting 125 µL (500 µg) of Streptavidin Magnetic Beads (New England Biolabs, Whitby, Canada) into a clean RNase-free microcentrifuge tube, and 100 µL of buffer [0.5 M NaCl, 20 mM Tris-HCl (pH 7.5), 1 mM EDTA] was added to the beads and they were then vortexed to suspend. A magnet was then applied to the side of tube for approximately 30 seconds, and the supernatant was removed and discarded. Next, 1.0 $A_{260}$ unit of the biotin-(miR-10a-5p fragment capture probe) was dissolved in in 500 µL of buffer [0.5 M NaCl, 20 mM Tris-HCl (pH 7.5), 1 mM EDTA] to a final concentration 8 pmol/µL. Next, 25 µL of the biotin-(miR-10a-5p fragment capture probe) solution was added to the prepared magnetic beads and vortexed to suspend the beads. This was then incubated at room temperature for 5 minutes with occasional agitation by hand, then a magnet was applied, and the supernatant was again removed and discarded. The beads were washed by adding 100 µL of buffer [0.5 M NaCl, 20 mM Tris-HCl (pH 7.5), 1 mM EDTA], vortexing to suspend, and then applying a magnet and discarding the supernatant. The beads were then washed a second time in the same manner.

Next, 25 µL of the total RNA purified from urine was mixed with 25 µL of buffer [1 M NaCl, 40 mM Tris-HCl (pH 7.5), 2 mM EDTA] and heated at 65° C. for 5 minutes then quickly chilled at 4° C. for 3 minutes. The total RNA sample was then added to the previously prepared magnetic beads. The mixture was vortexed to suspend the particles, then incubated at room temperature for 10 minutes with occasional agitation by hand. A magnet was then applied and the supernatant (containing the depleted RNA) was collected. Next, 100 µL of the buffer was again added to the beads, followed by vortexing to suspend the beads. Again, a magnet was applied and the supernatant (containing the depleted RNA) was collected. This process was then repeated, for a total of 3 collections of the depleted RNA. Finally, 100 µL of a cold low salt buffer [0.15 M NaCl, 20 mM Tris-HCl (pH 7.5), 1 mM EDTA] was added to beads, and vortexed to suspend. Again, a magnet was applied, and the supernatant was removed and collected. All the recovered supernatants were then pooled.

The miR-10a-5p fragment-depleted RNA can be assayed or further processed (e.g. preparation of a sequencing library) immediately or it can be purified prior to the assay. Multiple purification and concentration methods are possible, including through the use of silicon carbide columns, silica columns, gel electrophoresis or ethanol precipitation.

Example 3—Improved Ratio of Useful Data Obtained During Small RNA Next Generation Sequencing of Human Urine by Selectively Depleting the Highly Abundant miR-10a-5p Fragments Two 30 mL urine samples were collected into 50 cc Falcon tubes (BD Diagnostics, Mississauga, Canada) from 6 healthy donors (3 males and 3 females)—a total of 12 tubes were collected. Total RNA was then purified from the 30 mL of human urine using Norgen's Urine Total RNA Purification Maxi Kit (Slurry Format) (Cat #29600, Norgen Biotek Corp., Thorold, Canada) according to the provided protocol. Next, the miR-10a-5p fragment was depleted from one of the total RNA samples from each donor using the probe described in Example 1 and the method outlined in Example 2. The other sample from each donor was not depleted in order to be used as a control.

Samples of miR-10a-5p fragment-depleted RNA were then concentrated using Norgen's Urine Total RNA Purification Maxi Kit (Slurry Format) (Cat #29600, Norgen Biotek Corp., Thorold, Canada) with a slight modification to the first two steps in the provided protocol: 1) The miR-10a-5p fragment-depleted RNA was mixed with an equal volume of Lysis Buffer A; and 2) the resulting mixture was then mixed with an equal volume of 96-100% ethanol (for example, a 350 µL RNA sample depleted of miR-10a-5p was first mixed with 350 µL of Lysis Buffer A and then mixed with 700 µL of 96-100% ethanol). Subsequently, the provided protocol was followed as specified in the kit insert of Norgen's Urine Total RNA Purification Maxi Kit (Slurry Format) (Cat #29600, Norgen Biotek Corp., Thorold, Canada), starting with Step 3.

The concentrated miR-10a-5p fragment-depleted RNA from each donor was then used for small RNA library preparation for downstream NGS analysis. Briefly, using the NEBNext® Multiplex Small RNA Library Prep Set for Illumina® (New England Biolabs, Whitby, Canada), the RNA was first ligated to the 3' adapter, followed by RT primer hybridization and 3' adapter blocking. Next, the 5' adapter was ligated to the 5' end of the RNA, which was then reverse transcribed into cDNA. This was followed by a limited (15) cycle PCR amplification to enrich the cDNA and also to attach the indexing (barcode) sequences. The indexed libraries were then resolved on a 6% TBE gel and the fragments of interest excised from the gel, crushed and left over-night in 200 µL of water to release DNA. The crushed gel pieces were filtered out and the DNA was concentrated using Norgen's RNA Clean-Up and Concentration Micro-Elute Kit (Cat #61000, Norgen, Thorold, Canada) according to the provided protocol. All libraries were quantified and assessed for library size by the Agilent Bioanalyzer using the Agilent High Sensitivity DNA Kit (Agilent Technologies, Santa Clara, United States). As a control, the urine RNA isolated from each individual that was not depleted of the miR-10a-5p fragment was also used for small RNA library preparation.

Next, all of the small RNA libraries were sequenced on the Illumina NextSeq® (Illumina Inc., San Diego, United States) instrument according to the instructions provided by the manufacturer (Preparing Libraries for Sequencing on the NextSeq® and the NextSeq® System User Guide). The resulting NGS sequencing data was then analyzed in a number of different ways to verify that the ratio of useful data obtained was improved in the small RNA libraries prepared from urine that was depleted of miR-10a-5p compared to the control small RNA libraries prepared from non-depleted urine.

Figure 2:
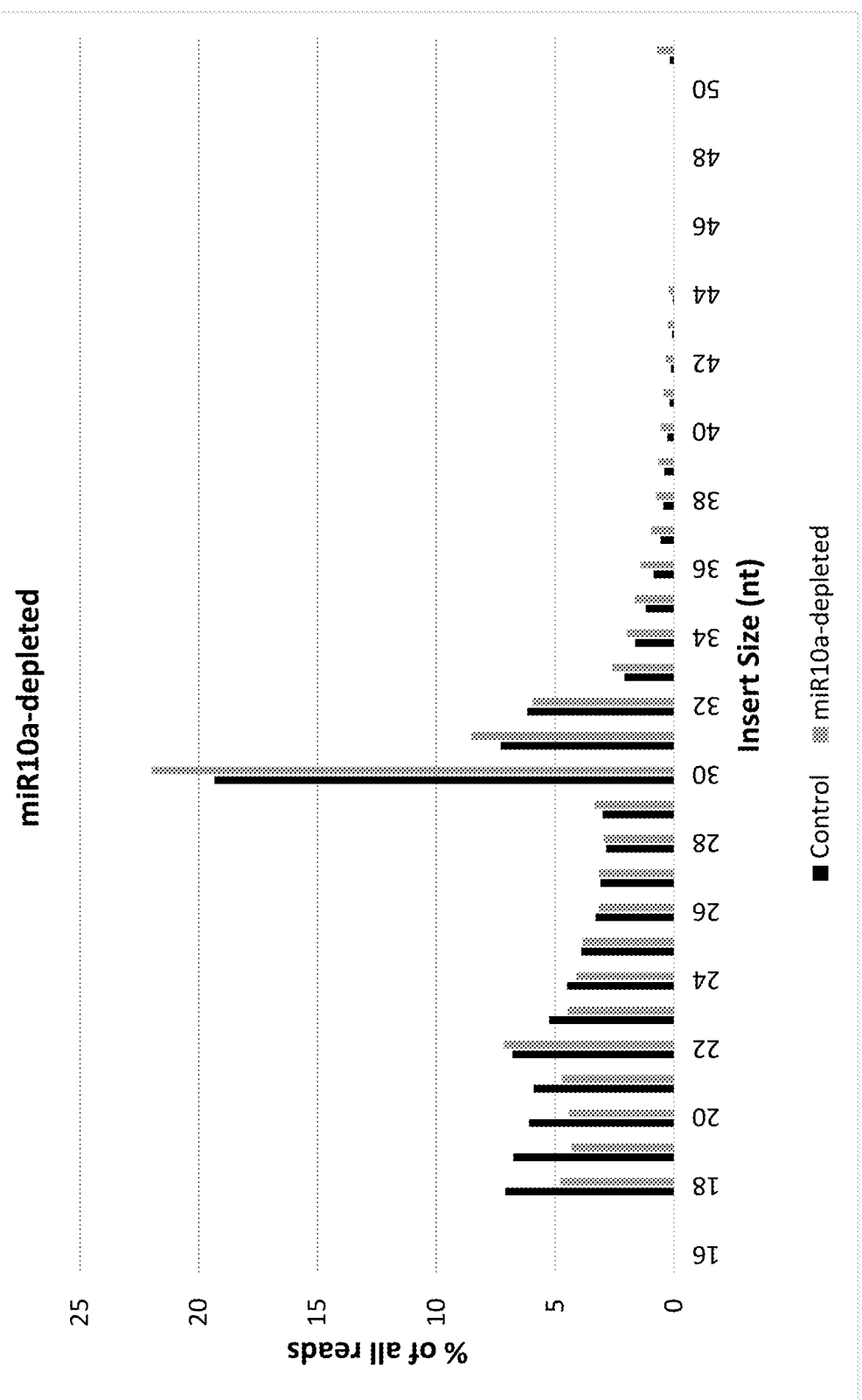
FIG. 2 is a graph that shows the correspondence between insert size and the overall % of reads for a control (non-depleted) urine RNA samples and miR-10a-5p fragment-depleted urine RNA sample from healthy donors.

The average number of reads per million mapped to miRNA was graphed for the control (non-depleted) and miR-10a-5p-depleted samples (FIG. 1). Depletion of miR-10a-5p increased the NGS run capacity towards other miRNA sequences and therefore enhanced run outcomes. The number of reads that represents miRNA sequences in an NGS library has increased after the depletion of miR-10a-5p. FIG. 2 illustrates the average number of reads graphed according to insert size incorporated into the library. When performing NGS of small RNA libraries from human urine, the main RNA of interest for analysis is miRNA, which are approximately 20 nt in size. The abundant miR-10a-5p fragment is 23 nt in size. Therefore, the depletion of the miR-10a-5p fragment can also be verified by determining the % of reads for each insert size. These results demonstrate that the method of the present invention improves the NGS run capacity.

Example 4—Preparation of Capture Probe for miR-10b-5p Fragment

The capture probe for the miR-10b-5p fragment was designed by using the "*Homo sapiens* miRNA 10b" (miR-Base accession: MIMAT0000254) as a reference sequence for the full length miR-10b-5p and creating a complement of the 23 nucleotides in the sequence. This was based on previous observations and sequencing data of small RNA purified form urine, which showed that the most over-represented sequence in the small RNA fraction of RNA purified from urine was the 23 nucleotide long miR-10b-5p.

The capture probe was designed to be the complement of the 23 base miR-10b-5p fragment having the sequence (SEQ ID NO: 3)
5'-UACCCUGUAGAACCGAAUUUGUG-3'.

The sequence of the oligonucleotide capture probe is:

(SEQ ID NO: 4)
5'-CACAAATTCGGTTCTACAGGGTA-3'.

In order to facilitate the removal of the miR-10b-5p: capture oligonucleotide complexes, biotin was covalently attached to the 5' end of the capture oligonucleotide.

Example 5—Depletion of the miR-10b-5p Fragment from Human Urine

A 30 mL urine sample was collected into a 50 cc Falcon tube (BD Diagnostics, Mississauga, Canada) from 6 healthy donors (3 males and 3 females). Total RNA was then purified from the 30 mL of the human urine using Norgen's Urine Cell-Free Circulating RNA Purification Maxi Kit (Cat #57100, Norgen Biotek Corp., Thorold, Canada) according to the provided protocol.

Next, the miR-10b-5p fragment was depleted from the total RNA sample using the probe described in Example 4. Briefly, Streptavidin Magnetic Beads were prepared by aliquoting 125 µL (500 µg) of Streptavidin Magnetic Beads (New England Biolabs, Whitby, Canada) into a clean RNase-free microcentrifuge tube, and 100 µL of buffer [0.5 M NaCl, 20 mM Tris-HCl (pH 7.5), 1 mM EDTA] was added to the beads and they were then vortexed to suspend. A magnet was then applied to the side of tube for approximately 30 seconds, and the supernatant was removed and discarded. Next, 1.0 $A_{260}$ unit of the biotin-(miR-10b-5p fragment capture probe) was dissolved in in 500 µL of buffer [0.5 M NaCl, 20 mM Tris-HCl (pH 7.5), 1 mM EDTA] to a final concentration 8 pmol/µL. Next, 25 µL of the biotin-(miR-10b-5p fragment capture probe) solution was added to the prepared magnetic beads and vortexed to suspend beads. This was then incubated at room temperature for 5 minutes with occasional agitation by hand, then a magnet was applied, and the supernatant was again removed and discarded. The beads were washed by adding 100 µL of buffer [0.5 M NaCl, 20 mM Tris-HCl (pH 7.5), 1 mM EDTA], vortexing to suspend, and then applying a magnet and discarding the supernatant. The beads were then washed a second time in the same manner.

Next, 25 µL of the total RNA purified from urine was mixed with 25 µL of buffer [1 M NaCl, 40 mM Tris-HCl (pH 7.5), 2 mM EDTA] and heated at 65° C. for 5 minutes then quickly chilled at 4° C. for 3 minutes. The total RNA sample was then added to the previously prepared magnetic beads. The mixture was vortexed to suspend the particles, then incubated at room temperature for 10 minutes with occasional agitation by hand. A magnet was then applied and the supernatant (containing the depleted RNA) was collected. Next, 100 µL of the buffer was again added to the beads, followed by vortexing to suspend the beads. Again, a magnet was applied and the supernatant (containing the depleted RNA) was collected. This process was then repeated, for a total of 3 collections of the depleted RNA. Finally, 100 µL of a cold low salt buffer [0.15 M NaCl, 20 mM Tris-HCl (pH 7.5), 1 mM EDTA] was added to beads, and vortexed to suspend. Again, a magnet was applied, and the supernatant was removed and collected. All of the recovered supernatants were then pooled.

The miR-10b-5p fragment-depleted RNA can be assayed or further processed (e.g. preparation of a sequencing library) immediately or it can be purified prior to the assay. Multiple purification and concentration methods are possible, including through the use of silicon carbide columns, silica columns, gel electrophoresis or ethanol precipitation.

Example 6—Improved Ratio of Useful Data Obtained During Small RNA Next Generation Sequencing of Human Urine by Selectively Depleting the Highly Abundant miR-10b-5p Fragments Two 30 mL urine samples were collected into 50 cc Falcon tubes (BD Diagnostics, Mississauga, Canada) from 6 healthy donors (3 males and 3 females)—a total of 12 tubes were collected. Total RNA was then purified from the 30 mL of the human urine using Norgen's Urine Total RNA Purification Maxi Kit (Slurry Format) (Cat #29600, Norgen Biotek Corp., Thorold, Canada) according to the provided protocol. Next, the miR-10b-5p fragment was depleted from one of the total RNA samples from each donor using the probe described in Example 4 and the method outlined in Example 5. The other sample from each donor was not depleted in order to be used as a control.

Samples of miR-10b-5p fragment-depleted RNA were then concentrated using Norgen's Urine Total RNA Purification Maxi Kit (Slurry Format) (Cat #29600, Norgen Biotek Corp., Thorold, Canada) with a slight modification to the first two steps in the provided protocol: 1) The miR-10a-5p fragment-depleted RNA was mixed with an equal volume of Lysis Buffer A; and 2) the resulting mixture was then mixed with an equal volume of 96-100% ethanol (for example, a 350 µL RNA sample depleted of miR-10a-5p was first mixed with 350 µL of Lysis Buffer A and then mixed with 700 µL of 96-100% ethanol). Subsequently, the provided protocol was followed as specified in the kit insert of Norgen's Urine Total RNA Purification Maxi Kit (Slurry Format) (Cat #29600, Norgen Biotek Corp., Thorold, Canada), starting with Step 3.

The concentrated miR-10b-5p fragment-depleted RNA from each donor was then used for small RNA library preparation for downstream NGS analysis. Briefly, using the NEBNext® Multiplex Small RNA Library Prep Set for Illumina® (New England Biolabs, Whitby, Canada), the RNA was first ligated to the 3'adapter, followed by RT primer hybridization and 3' adapter blocking. Next, the 5'adapter was ligated to the 5' end of the RNA, which was then reverse transcribed into cDNA. This was followed by a limited (15) cycle PCR amplification to enrich the cDNA and also to attach the indexing (barcode) sequences. The indexed libraries were then resolved on a 6% TBE gel and the fragments of interest excised from the gel, crushed and left over-night in 200 µL of water to release DNA. The crushed gel pieces were filtered out and the DNA in the filtrate concentrated using Norgen's RNA Clean-Up and Concentration Micro-Elute Kit (Cat #61000, Norgen, Thorold, Canada) according to the provided protocol. All libraries were quantified and assessed for library size by the Agilent Bioanalyzer using the Agilent High Sensitivity DNA Kit (Agilent Technologies, Santa Clara, United States). As a control, the urine RNA isolated from each individual that was not depleted of the miR-10b-5p fragment was also used for small RNA library preparation.

Next, all of the small RNA libraries were sequenced on the Illumina NextSeq® (Illumina Inc., San Diego, United States) instrument according to the instructions provided by the manufacturer (Preparing Libraries for Sequencing on the NextSeq® and the NextSeq® System User Guide). The resulting NGS sequencing data was then analyzed in a number of different ways to verify that the ratio of useful data obtained was improved in the small RNA libraries prepared from urine that was depleted of the 5' fragment of miR-10b-5p compared to the control small RNA libraries prepared from non-depleted urine.

Figure 3:
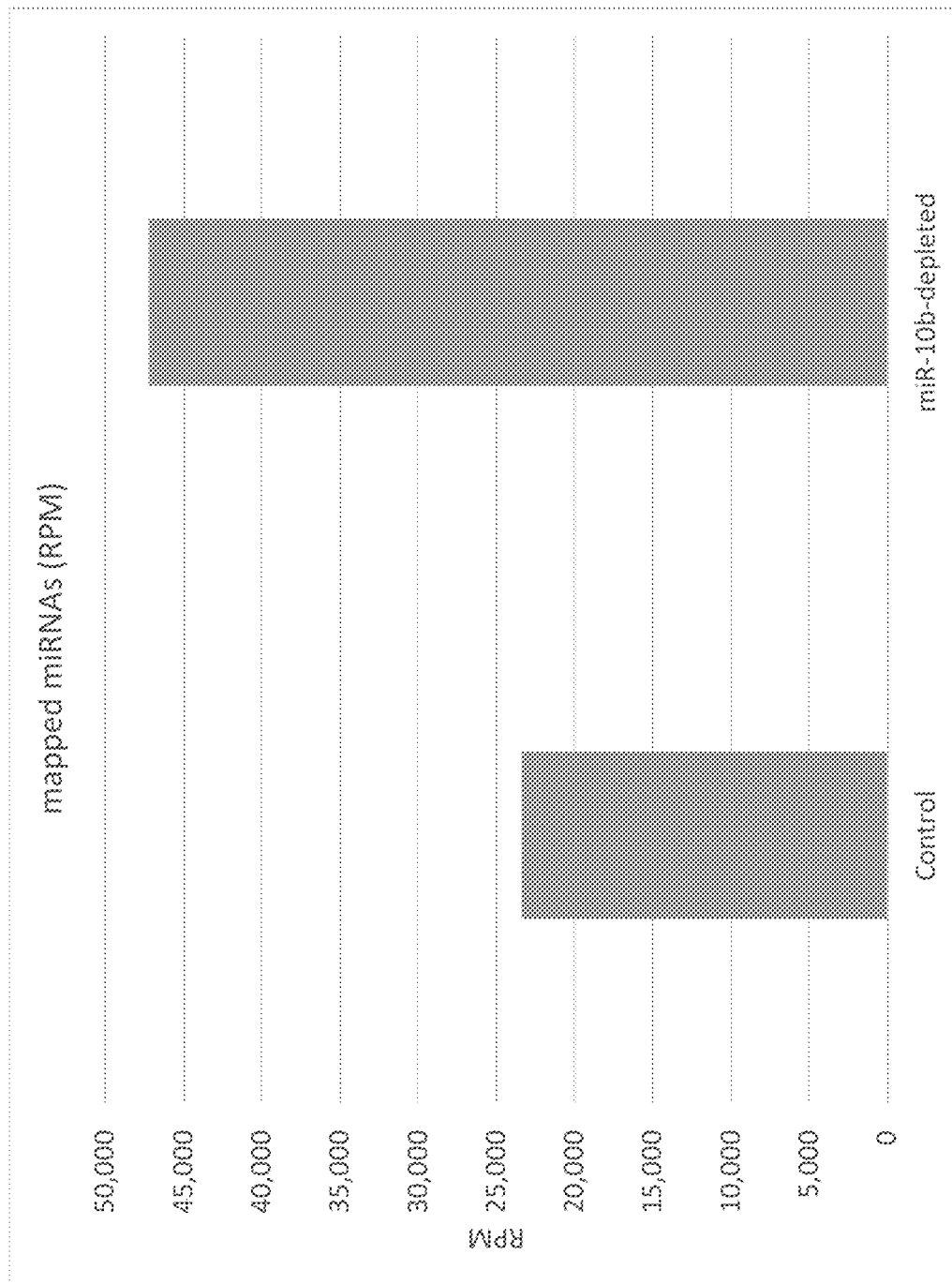
FIG. 3 is a graph that shows the number of read per million (RPM) mapped miRNAs over all clipped reads for a control (non-depleted) urine RNA sample and miR-10b-5p fragment-depleted urine RNA samples from healthy donors.
Figure 4:
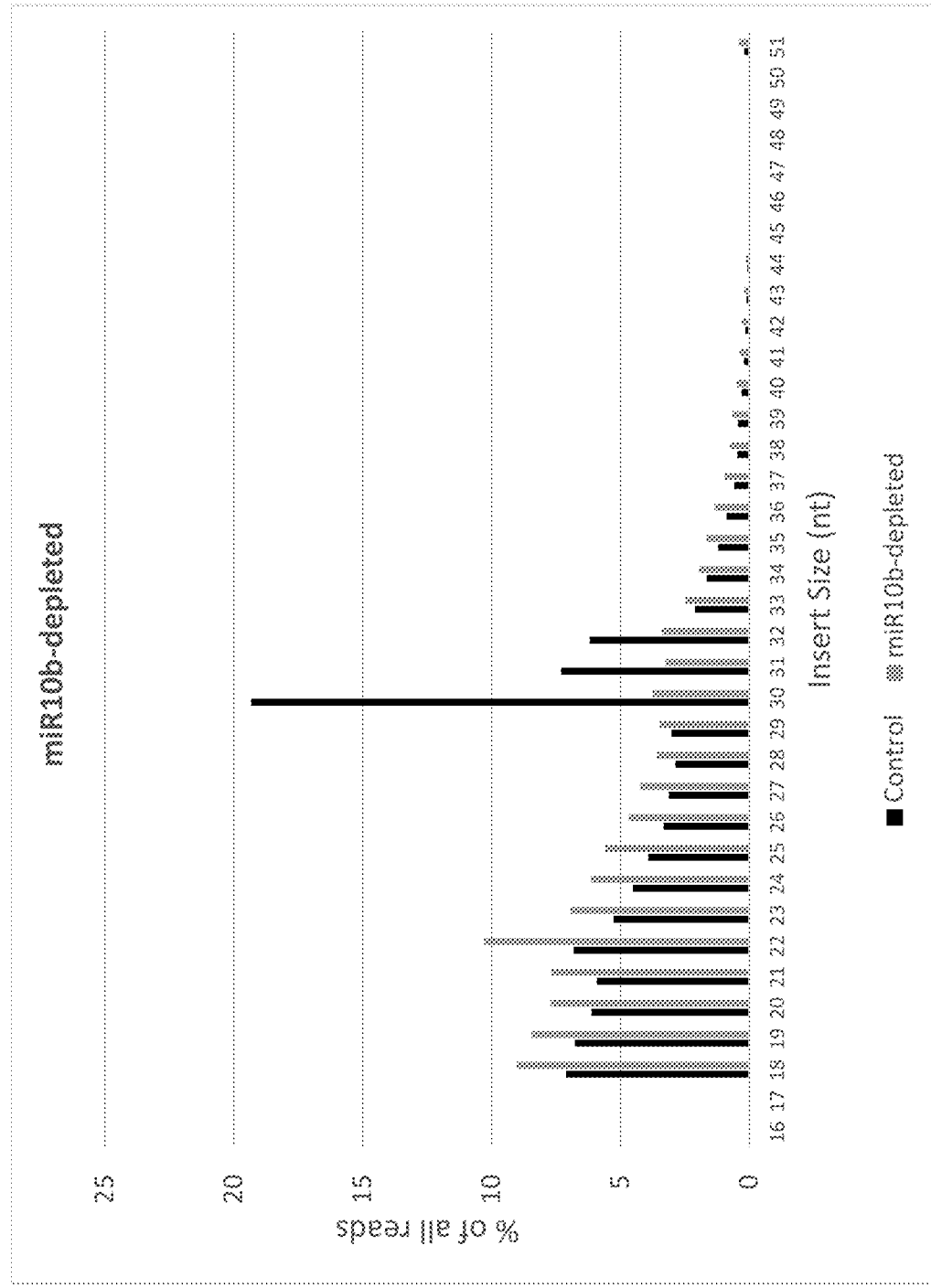
FIG. 4 is a graph that shows the correspondence between insert size and the overall % of reads for a control (non-depleted) urine RNA sample and miR-10b-5p fragment-depleted urine RNA samples from healthy donors.
Figure 5:
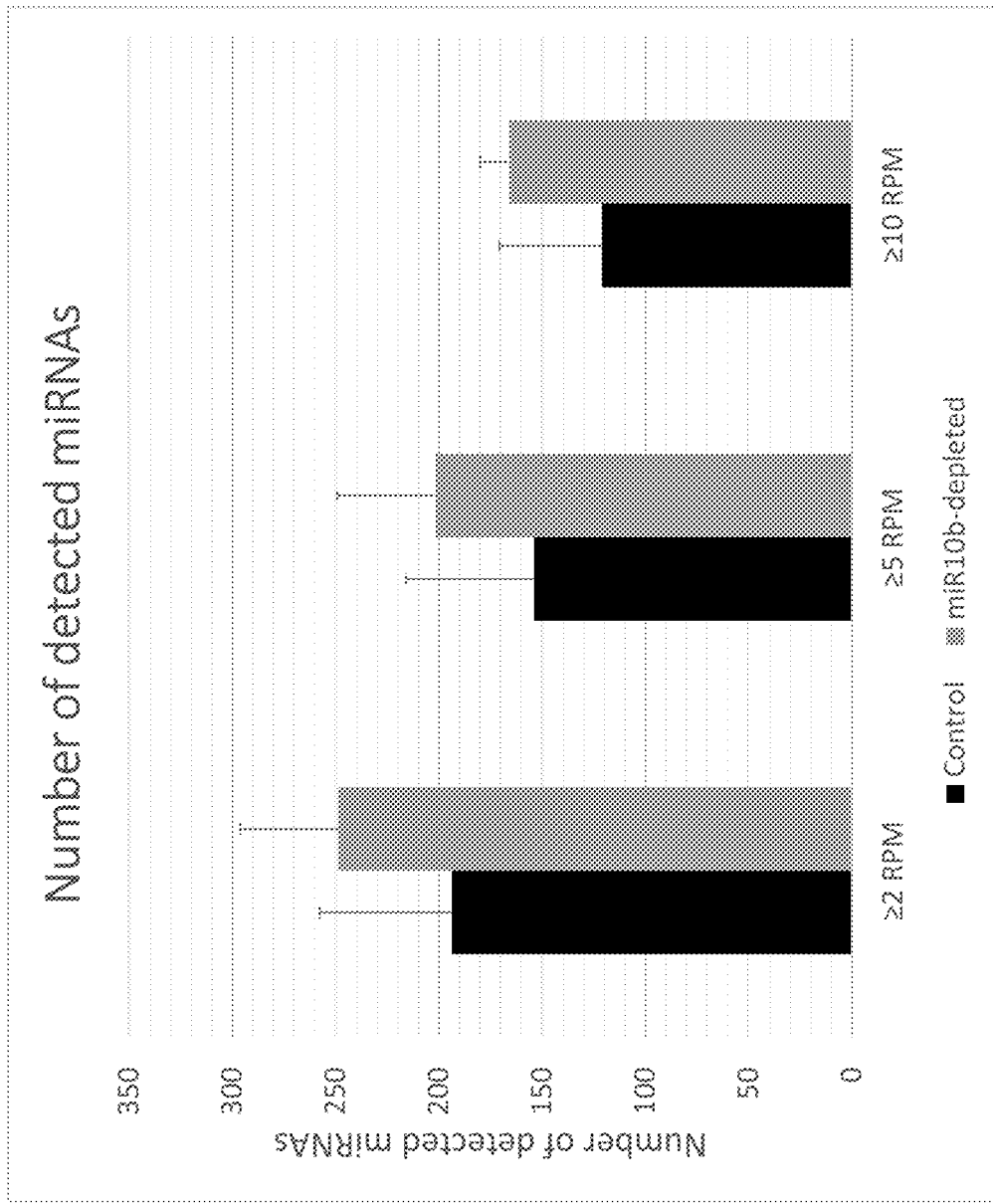
FIG. 5 is a graph depicting the average number of miRNA detected in NGS runs from libraries created from both control (non-depleted) urine RNA, as well as the miR-10b-5p fragment-depleted urine RNA samples.

The average number of reads per million mapped to miRNA was graphed for the control (non-depleted) and miR-10b-5p-depleted samples (FIG. 3). Depletion of miR-10b-5p increased the NGS run capacity towards other miRNA sequences and therefore enhanced run outcomes. The number of reads that represents miRNA sequences in an NGS library has increased after the depletion of miR-10b-5p. FIG. 4 illustrates the average number of reads graphed according to insert size incorporated into the library. When performing NGS of small RNA libraries from urine, the main RNA of interest for analysis is miRNA, which are approximately 20 nt in size. The abundant miR-10b-5p fragment is 23 nt in size. Therefore, the depletion of the miR-10b-5p fragment can also be verified by determining the % of reads for each insert size. FIG. 5 is a graph depicting the average number of miRNA detected in NGS runs from libraries created from both control (non-depleted) urine RNA, as well as the miR-10b-5p fragment-depleted urine RNA. Three minimum counts cut-offs were used to consider a miRNA detectable: 2 counts, 5 counts and 10 counts. The number of detected miRNAs was increased upon miR-10b-5p depletion by 45, 48 and 55 miRNAs at the three detection cut-off reads used (2, 5 and 10 counts, respectively), with 28-37% increase in numbers of detected miRNAs. Fragment-depletion resulted in a greater sensitivity of miRNA detection because of increased sequencing depth. These results demonstrate that the method of the present invention improves the signal-to-noise ratio and allows for more low-abundance miRNAs to be detected during NGS applications.

Example 7—Depletion of the miR-10b-5p and miR-10b-5p Fragments from Human Urine

A 30 mL urine sample was collected into a 50 cc Falcon tube (BD Diagnostics, Mississauga, Canada) from 6 healthy donors (3 males and 3 females). Total RNA was then purified from the 30 mL of the human urine using Norgen's Urine Cell-Free Circulating RNA Purification Maxi Kit (Cat #57100, Norgen Biotek Corp., Thorold, Canada) according to the provided protocol.

Next, both the miR10a-5p and miR-10b-5p fragment were depleted from the total RNA sample using the probes described in Examples 1 and 4. Briefly, Streptavidin Magnetic Beads were prepared by aliquoting 125 µL (500 µg) of Streptavidin Magnetic Beads (New England Biolabs, Whitby, Canada) into a clean RNase-free microcentrifuge tube, and 100 µL of buffer [0.5 M NaCl, 20 mM Tris-HCl (pH 7.5), 1 mM EDTA] was added to the beads and they were then vortexed to suspend. A magnet was then applied to the side of tube for approximately 30 seconds, and the supernatant was removed and discarded. Next, 1.0 $A_{260}$ unit of the biotin-(miR10a-5p and miR-10b-5p fragment capture probe) was dissolved in in 500 µL of buffer [0.5 M NaCl, 20 mM Tris-HCl (pH 7.5), 1 mM EDTA] to a final concentration 8 pmol/µL. Next, 25 µL of the biotin-(miR10a-5p and miR-10b-5p fragment capture probe) solution was added to the prepared magnetic beads and vortexed to suspend beads. This was then incubated at room temperature for 5 minutes with occasional agitation by hand, then a magnet was applied, and the supernatant was again removed and discarded. The beads were washed by adding 100 µL of buffer [0.5 M NaCl, 20 mM Tris-HCl (pH 7.5), 1 mM EDTA], vortexing to suspend, and then applying a magnet and discarding the supernatant. The beads were then washed a second time in the same manner.

Next, 25 µL of the total RNA purified from urine was mixed with 25 µL of buffer [1 M NaCl, 40 mM Tris-HCl (pH 7.5), 2 mM EDTA] and heated at 65° C. for 5 minutes then quickly chilled at 4° C. for 3 minutes. The total RNA sample was then added to the previously prepared magnetic beads. The mixture was vortexed to suspend the particles, then incubated at room temperature for 10 minutes with occasional agitation by hand. A magnet was then applied and the supernatant (containing the depleted RNA) was collected. Next, 100 µL of the buffer was again added to the beads, followed by vortexing to suspend the beads. Again, a magnet was applied and the supernatant (containing the depleted RNA) was collected. This process was then repeated, for a total of 3 collections of the depleted RNA. Finally, 100 µL of a cold low salt buffer [0.15 M NaCl, 20 mM Tris-HCl (pH 7.5), 1 mM EDTA] was added to beads, and vortexed to suspend. Again, a magnet was applied, and the supernatant was removed and collected. All the recovered supernatants were then pooled.

The miR10a-5p and miR-10b-5p fragment-depleted RNA can be assayed or further processed (e.g. preparation of a sequencing library) immediately or it can be purified prior to the assay. Multiple purification and concentration methods are possible, including through the use of silicon carbide columns, silica columns, gel electrophoresis or ethanol precipitation.

Example 8—Improved Ratio of Useful Data Obtained During Small RNA Next Generation Sequencing of Human Urine by Selectively Depleting the Highly Abundant miR10a-5p and miR-10b-5p Fragments Two 30 mL urine samples were collected into 50 cc Falcon tubes (BD Diagnostics, Mississauga, Canada) from 6 healthy donors (3 males and 3 females), a total of 12 tubes were collected. Total RNA was then purified from the 30 mL of the human urine using Norgen's Urine Total RNA Purification Maxi Kit (Slurry Format) (Cat #29600, Norgen Biotek Corp., Thorold, Canada) according to the provided protocol. Next, the miR10a-5p and miR-10b-5p fragments were depleted from one of the total RNA samples from each donor using the probes described in Example 1 and 4, and the method outlined in Example 7. The other sample from each donor was not depleted in order to be used as a control.

Samples of miR-10a-5p and miR-10b-5p fragments-depleted RNA were then concentrated using Norgen's Urine Total RNA Purification Maxi Kit (Slurry Format) (Cat #29600, Norgen Biotek Corp., Thorold, Canada) with a slight modification to the first two steps in the provided protocol: 1) The miR-10a-5p and miR-10b-5p fragments-depleted RNA was mixed with an equal volume of Lysis Buffer A; and 2) the resulting mixture was then mixed with an equal volume of 96-100% ethanol (for example, a 350 µL RNA sample depleted of miR-10a-5p and miR-10b-5p was first mixed with 350 µL of Lysis Buffer A and then mixed with 700 µL of 96-100% ethanol). Subsequently, the provided protocol was followed as specified in the kit insert of Norgen's Urine Total RNA Purification Maxi Kit (Slurry Format) (Cat #29600, Norgen Biotek Corp., Thorold, Canada), starting with Step 3.

The concentrated miR-10a-5p and miR-10b-5p fragment-depleted RNA from each donor was then used for small RNA library preparation for downstream NGS analysis. Briefly, using the NEBNext® Multiplex Small RNA Library Prep Set for Illumina® (New England Biolabs, Whitby, Canada), the RNA was first ligated to the 3'adapter, followed by RT primer hybridization and 3' adapter blocking. Next, the 5'adapter was ligated to the 5' end of the RNA, which was then reverse transcribed into cDNA. This was followed by a limited (15) cycle PCR amplification to enrich the cDNA and also to attach the indexing (barcode) sequences. The indexed libraries were then resolved on a 6% TBE gel and the fragments of interest excised from the gel, crushed and left over-night in 200 µL of water to release DNA. The crushed gel pieces were filtered out and the DNA in the filtrate concentrated using Norgen's RNA Clean-Up and Concentration Micro-Elute Kit (Cat #61000, Norgen, Thorold, Canada) according to the provided protocol. All libraries were quantified and assessed for library size by the Agilent Bioanalyzer using the Agilent High Sensitivity DNA Kit (Agilent Technologies, Santa Clara, United States). As a control, the urine RNA isolated from each individual that was not depleted of the miR10a-5p and miR-10b-5p fragment was also used for small RNA library preparation.

Next, all of the small RNA libraries were sequenced on the Illumina NextSeq® (Illumina Inc., San Diego, United States) instrument according to the instructions provided by the manufacturer (Preparing Libraries for Sequencing on the NextSeq® and the NextSeq® System User Guide). The resulting NGS sequencing data was then analyzed in a number of different ways to verify that the ratio of useful data obtained was improved in the small RNA libraries prepared from urine that was depleted of the miR10a-5p and miR-10b-5p compared to the control small RNA libraries prepared from non-depleted urine.

Figure 6:
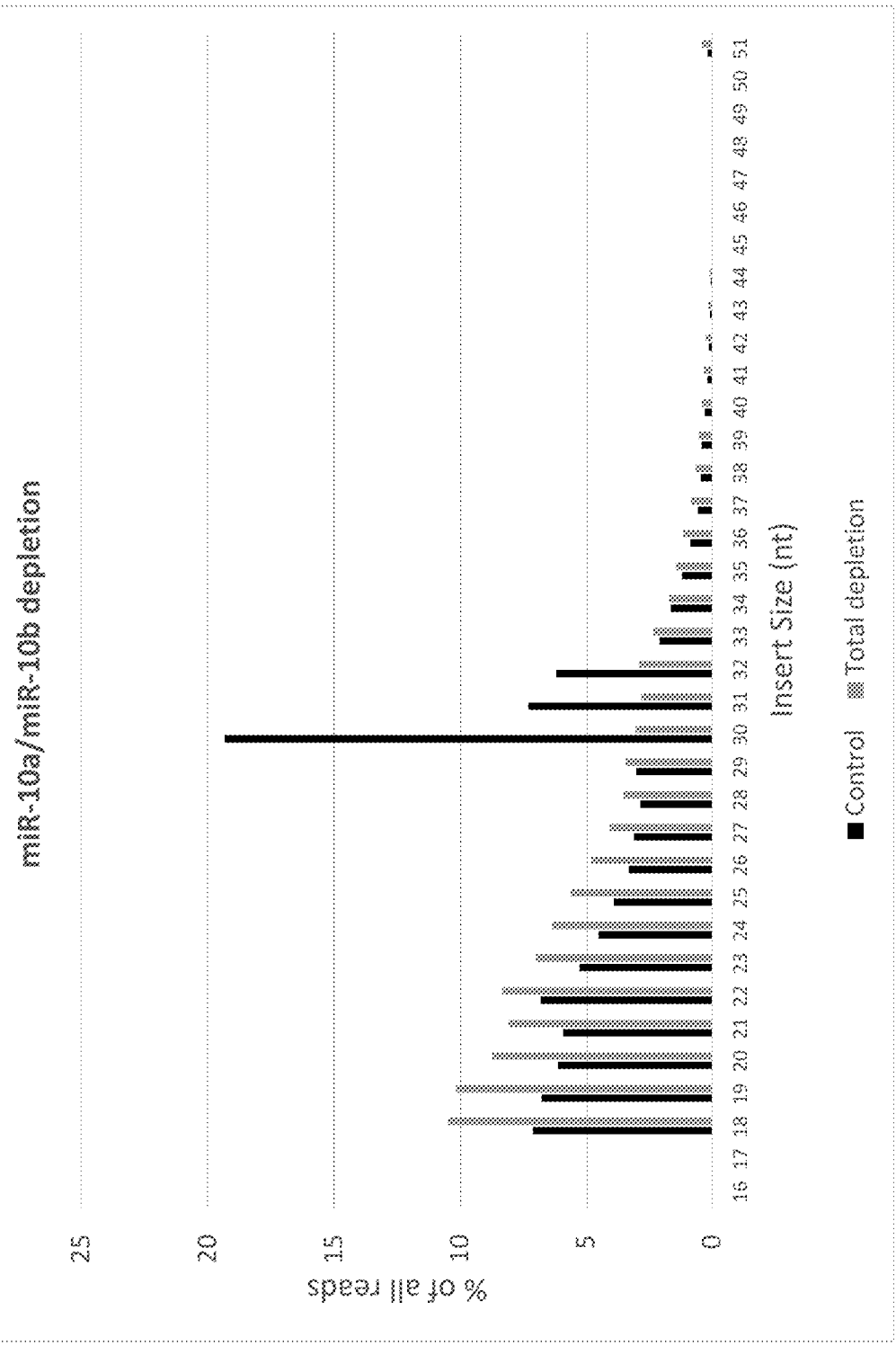
FIG. 6 is a graph of insert sizes that shows the correspondence between insert size and the overall % of reads for a control (non-depleted) urine RNA sample and both miR-10a-5p and miR-10b-5p fragments-depleted urine RNA samples from healthy donors.
Figure 7:
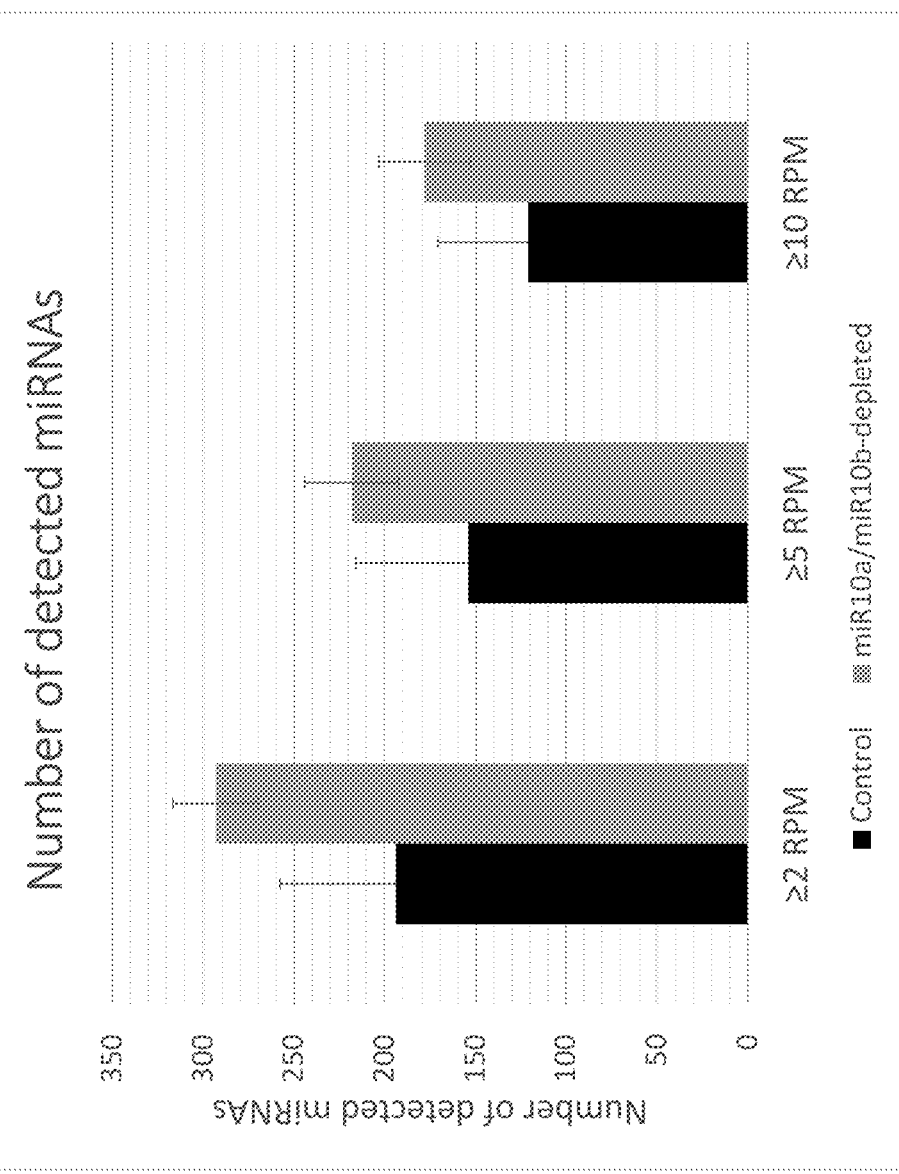
FIG. 7 is a graph depicting the average number of miRNA detected in NGS runs from libraries created from both control (non-depleted) urine RNA, as well as both miR-10a-5p and miR-10b-5p fragments-depleted urine RNA samples.

FIG. 6 illustrates the average number of reads graphed according to insert size incorporated into the library. When performing NGS of small RNA libraries from human urine, the main RNA of interest for analysis is miRNA, which are approximately 20 nt in size. The abundant miR10a-5p and miR-10b-5p fragments are 23 nt in size. Therefore, the depletion of the miR10a-5p and miR-10b-5p fragments can also be verified by determining the % of reads for each insert size. FIG. 7 is a graph depicting the average number of miRNA detected in NGS runs from libraries created from both control (non-depleted) urine RNA, as well as the miR10a-5p and miR-10b-5p fragment-depleted urine RNA. Three minimum counts cut-offs were used to consider a miRNA detectable: 2 counts, 5 counts and 10 counts. The number of detected miRNAs was increased upon miR10a-5p and miR-10b-5p depletion by 99, 64 and 57 miRNAs at the three detection cut-off reads used (2, 5 and 10 counts, respectively), with 41-51% increase in numbers of detected miRNAs. Fragment-depletion resulted in a greater sensitivity of miRNA detection because of increased sequencing depth. These results demonstrate that the method of the present invention improves the signal-to-noise ratio and allows for more low-abundance miRNAs to be detected during NGS applications.

REFERENCES

Abdelmaksoud-Dammak R, Chamtouri N, Triki M, Saadallah-Kallel A, Ayadi W, Charfi S, et al. *Overexpression of miR-10b in colorectal cancer patients: Correlation with TWIST-1 and E-cadherin expression*. Tumor Biol. 2017 39(3):1010428317695916.

Arai T, Okato A, Kojima S, Idichi T, Koshizuka K, Kurozumi A, et al. *Regulation of spindle and kinetochore-associated protein 1 by antitumor miR-10a-5p in renal cell carcinoma*. Cancer Science 2017; 108(10): 2088-2101.

El-Mogy M., Lam B., Haj-Ahmad T.A., McGowan S., Yu D., Nosal L., et al. *Diversity and signature of small RNA in different bodily fluids using next generation sequencing*. BMC Genomics. 2018; 19:408.

Ma Z, Chen Y, Min L, Li L, Huang H, Li J, et al. *Augmented miR-10b expression associated with depressed expression of its target gene KLF4 involved in gastric carcinoma*. Int. J. Clin. Exp. Pathol. 2015; 8:5071-9.

Veerla S, Lindgren D, Kvist A, Frigyesi A, Staaf J, Persson H, et al. *miRNA expression in urothelial carcinomas: Important roles of miR-10a, miR-222, miR-125b, miR-7 and miR-452 for tumor stage and metastasis, and frequent homozygous losses of miR-31*. Int. J. Cancer 2009; 124: 2236-2242.

Xiao H, Li H, Yu G, Xiao W, Hu J, Tang K, et al. *MicroRNA-10b promotes migration and invasion through KLF4 and HOXD10 in human bladder cancer*. Oncol. Rep. 2014; 31:1832-8.

Zhang L, Sun J, Wang B, Ren J C, Su W, Zhang T. *MicroRNA-10b Triggers the Epithelial-Mesenchymal Transition (EMT) of Laryngeal Carcinoma Hep-2 Cells by Directly Targeting the E-cadherin*. Appl. Biochem. Biotechnol. 2015; 176:33-44.

Zhou K, Spillman M A, Behbakht K, Komatsu J M, Abrahante J E, Hicks D, et al. *A method for extracting and characterizing RNA from urine: For downstream PCR and RNAseq analysis*. Anal. Biochem. 2017; 536:8-15.

The invention claimed is:

1. A method of improving global gene expression analysis for a population of RNA molecules derived from human urine, the method comprising the step of depleting miR-10a-5p fragments and/or miR-10b-5p fragments from the population of RNA molecules, wherein the step of depleting miR-10a-5p fragments and/or miR-10b-5p fragments from the population of RNA molecules comprises:

adding miR-10a-5p specific oligonucleotide probes and/or miR-10b-5p specific oligonucleotide probes to a sample containing the population of RNA molecules, wherein each miR-10a-5p specific oligonucleotide probe comprises a nucleotide sequence that is the complement to a nucleotide sequence of miR-10a-5p and each miR-10b-5p specific oligonucleotide probe comprises a nucleotide sequence that is the complement to a nucleotide sequence of miR-10b-5p;

forming a complex between one or more miR-10a-5p fragments and a miR-10a-5p specific oligonucleotide probe and/or forming a complex between one or more miR-10b-5p fragments and a miR-10b-5p specific oligonucleotide probe; and removing the miR-10a-5p:oligonucleotide complexes and/or the miR-10b-5p:oligonucleotide complexes from the sample, wherein the remaining sample contains a miR-10a-5p and/or miR-10b-5p depleted population of small RNA molecules;

wherein the step of removing the miR-10a-5p:oligonucleotide complexes and/or miR-10b-5p:oligonucleotide complexes from the sample comprises:

combining the sample with a binding buffer, an alcohol and a silicon carbide slurry to provide a binding mixture, wherein the alcohol concentration of the binding mixture is about 1-30% (v/v) to affect selective binding of the miR-10a-5p:oligonucleotide complexes and/or miR-10b-5p:oligonucleotide complexes to the silicon carbide;

removing the miR-10a-5p:oligonucleotide complex and/or miR-10b-5p:oligonucleotide complex bound silicon carbide from the sample; and collecting the remaining sample containing the miR-10a-5p and/or miR-10b-5p depleted population of small RNA molecules.

2. The method of claim 1, wherein the alcohol is ethanol and the alcohol concentration of the binding mixture is about 1-10% (v/v).

3. The method of claim 1, wherein each miR-10a-5p specific oligonucleotide probe comprises multiple copies of the nucleotide sequence that is the complement to the nucleotide sequence of miR-10a-5p and each miR-10b-5p specific oligonucleotide probe comprises multiple copies of the nucleotide sequence that is the complement to the nucleotide sequence of miR-10b-5p.

4. The method of claim 1, wherein the nucleotide sequence of miR-10a-5p has at least 90% identity to the nucleotide sequence of SEQ ID NO: 1 and wherein the nucleotide sequence of miR-10b-5p has at least 90% identity to the nucleotide SEQ ID NO: 3.

5. The method of claim 1, wherein the miR-10a-5p specific oligonucleotide probe has at least 90% identity to the nucleotide sequence of SEQ ID NO: 2 and the miR-10b-5p specific oligonucleotide probe has at least 90% identity to the nucleotide sequence of SEQ ID NO: 4.

6. The method of claim 1, wherein the global gene expression analysis is next generation sequencing and wherein the method further comprises the steps of:
preparing a library using the remaining sample; and
sequencing the library.

7. A method of improving global gene expression analysis for a population of RNA molecules derived from human urine, the method comprising the step of depleting miR-10a-5p fragments and/or miR-10b-5p fragments from the population of RNA molecules, wherein the step of depleting miR-10a-5p fragments and/or miR-10b-5p fragments from the population of RNA molecules comprises:
adding miR-10a-5p specific oligonucleotide probes and/or miR-10b-5p specific oligonucleotide probes to a sample containing the population of RNA molecules, wherein each miR-10a-5p specific oligonucleotide probe comprises a nucleotide sequence that is the complement to a nucleotide sequence of miR-10a-5p and each miR-10b-5p specific oligonucleotide probe comprises a nucleotide sequence that is the complement to a nucleotide sequence of miR-10b-5p;

forming a complex between one or more miR-10a-5p fragments and a miR-10a-5p specific oligonucleotide probe and/or forming a complex between one or more miR-10b-5p fragments and a miR-10b-5p specific oligonucleotide probe; and removing the miR-10a-5p:oligonucleotide complexes and/or the miR-10b-5p:oligonucleotide complexes from the sample, wherein the remaining sample contains a miR-10a-5p and/or miR-10b-5p depleted population of small RNA molecules;

wherein the step of removing the miR-10a-5p:oligonucleotide complexes and/or miR-10b-5p:oligonucleotide complexes comprises:

combining the sample with a binding buffer and alcohol to provide a binding mixture;

applying the binding mixture to a silicon carbide column, wherein the alcohol concentration of the binding mixture is about 1-30% (v/v) to affect selective binding of the miR-10a-5p:oligonucleotide complexes and/or miR-10b-5p:oligonucleotide complexes to the silicon carbide;

collecting the column flowthrough containing the miR-10a-5p and/or miR-10b-5p depleted population of small RNA molecules.

8. The method of claim 7, wherein the alcohol is ethanol and the alcohol concentration of the binding mixture is about 1-10% (v/v).

9. The method of claim 7, wherein each miR-10a-5p specific oligonucleotide probe comprises multiple copies of the nucleotide sequence that is the complement to the nucleotide sequence of miR-10a-5p and each miR-10b-5p specific oligonucleotide probe comprises multiple copies of the nucleotide sequence that is the complement to the nucleotide sequence of miR-10b-5p.

10. The method of claim 7, wherein the nucleotide sequence of miR-10a-5p has at least 90% identity to the nucleotide sequence of SEQ ID NO: 1 and wherein the nucleotide sequence of miR-10b-5p has at least 90% identity to the nucleotide SEQ ID NO: 3.

11. The method of claim 7, wherein the miR-10a-5p specific oligonucleotide probe has at least 90% identity to the nucleotide sequence of SEQ ID NO: 2 and the miR-10b-5p specific oligonucleotide probe has at least 90% identity to the nucleotide sequence of SEQ ID NO: 4.

12. The method of claim 7, wherein the global gene expression analysis is next generation sequencing and wherein the method further comprises the steps of:
preparing a library using the remaining sample; and
sequencing the library.

\* \* \* \* \*